(12) United States Patent
Jiang et al.

(10) Patent No.: US 7,430,046 B2
(45) Date of Patent: Sep. 30, 2008

(54) PATHOGEN AND PARTICLE DETECTOR SYSTEM AND METHOD

(75) Inventors: Jian-Ping Jiang, Tucson, AZ (US);
John Babico, Oro Valley, AZ (US);
Michael Morrell, Tucson, AZ (US)

(73) Assignee: Biovigilant Systems, Inc., Tucson, AZ (US)

(*) Notice: Subject to any disclaimer, the term of this patent is extended or adjusted under 35 U.S.C. 154(b) by 0 days.

(21) Appl. No.: 11/193,204

(22) Filed: Jul. 29, 2005

(65) Prior Publication Data

US 2007/0013910 A1 Jan. 18, 2007

Related U.S. Application Data

(60) Provisional application No. 60/683,534, filed on May 20, 2005, provisional application No. 60/606,212, filed on Sep. 1, 2004, provisional application No. 60/592,619, filed on Jul. 30, 2004, provisional application No. 60/592,618, filed on Jul. 30, 2004.

(51) Int. Cl.
*G01N 15/02* (2006.01)
(52) U.S. Cl. ............... 356/336; 356/338; 356/443; 356/73
(58) Field of Classification Search ......... 356/335–343, 356/73, 39
See application file for complete search history.

(56) References Cited

U.S. PATENT DOCUMENTS 3,457,407 A * 7/1969 Goldberg ............... 250/373
3,710,933 A * 1/1973 Fulwyler et al. ......... 209/3.1
3,826,364 A * 7/1974 Bonner et al. ........... 209/3.1

(Continued)

FOREIGN PATENT DOCUMENTS

EP 0 214 769 8/1986

(Continued)

OTHER PUBLICATIONS

"Continuous, Rapid Biological Aerosol Detection with the Use of Fluorescence: Outdoor Test Results" Eversole et al., Field Analytical Chemistry and Technology 3(4-5):249-259, 1999.

(Continued)

*Primary Examiner*—Hoa Q Pham
(74) *Attorney, Agent, or Firm*—Hayes Soloway P.C.

(57) ABSTRACT

A particle detector has a sample area of cross section no in excess of about 2 mm for containing environmental fluid, a light source on one side of the sample area for directing a collimated or nearly collimated beam of light through the sample air or water so that part of the light beam will be scattered by any particles present in the air or water while the remainder remains unscattered, and a beam diverting device on the opposite side of the sample area for diverting or blocking at least the unscattered portion of the beam of light and directing at least part of the scattered light onto a detector. The detector produces output pulses in which each pulse has a height proportional to particle size and a pulse height discriminator obtains the size distribution of airborne particles detected in the air or water sample at a given time from the detector output. The detector may also include a device for discriminating between biological agents and inorganic particles.

28 Claims, 22 Drawing Sheets

U.S. PATENT DOCUMENTS

| | | | |
|---|---|---|---|
| 3,845,480 A | 10/1974 | Steinberg | 340/236 |
| 3,850,525 A * | 11/1974 | Kaye | 356/73 |
| 3,867,640 A | 2/1975 | Paulsen | 250/573 |
| 4,175,865 A | 11/1979 | Horvath et al. | 356/338 |
| 4,226,533 A | 10/1980 | Snowman et al. | 356/338 |
| 4,286,876 A | 9/1981 | Hogg et al. | 356/343 |
| 4,348,111 A | 9/1982 | Goulas et al. | 356/336 |
| 4,355,897 A * | 10/1982 | Kaye | 356/338 |
| 4,583,859 A | 4/1986 | Hall, II | 356/438 |
| 4,599,307 A * | 7/1986 | Saunders et al. | 435/34 |
| 4,728,190 A | 3/1988 | Knollenberg | 356/336 |
| 4,737,648 A | 4/1988 | Smith et al. | 250/560 |
| 4,830,494 A | 5/1989 | Ishikawa et al. | 356/336 |
| 4,839,529 A | 6/1989 | Fruengel | 250/574 |
| 4,940,326 A | 7/1990 | Tatsuno | 356/336 |
| 5,006,986 A | 4/1991 | Inoue | 364/413 |
| 5,056,918 A * | 10/1991 | Bott et al. | 356/336 |
| 5,083,865 A | 1/1992 | Kinney et al. | 356/338 |
| 5,085,500 A | 2/1992 | Blesener | 356/338 |
| 5,101,113 A | 3/1992 | Hirleman, Jr. et al. | 250/574 |
| 5,117,357 A | 5/1992 | Inoue | 364/413 |
| 5,121,988 A | 6/1992 | Blesener et al. | 356/442 |
| 5,123,731 A | 6/1992 | Yoshinaga et al. | 356/73 |
| 5,125,737 A | 6/1992 | Rodriguez et al. | 356/39 |
| 5,132,548 A | 7/1992 | Borden et al. | 250/574 |
| 5,166,537 A | 11/1992 | Horiuchi et al. | 250/573 |
| 5,180,065 A | 1/1993 | Touge et al. | 209/577 |
| 5,231,378 A | 7/1993 | Dennis et al. | 340/630 |
| 5,257,087 A | 10/1993 | Furuya | 356/336 |
| 5,266,798 A | 11/1993 | Borden et al. | 250/239 |
| 5,286,452 A | 2/1994 | Hansen | 422/73 |
| 5,305,072 A | 4/1994 | Sawada et al. | 356/336 |
| 5,315,115 A | 5/1994 | Gerber | 250/338 |
| 5,366,858 A | 11/1994 | Koizumi et al. | 435/5 |
| 5,383,024 A | 1/1995 | Maxey et al. | 356/336 |
| 5,408,307 A * | 4/1995 | Yamamoto et al. | 356/73 |
| 5,416,580 A | 5/1995 | Trainer | 356/336 |
| 5,426,501 A | 6/1995 | Hokanson et al. | 356/335 |
| 5,428,964 A | 7/1995 | Lobdell | 62/176 |
| 5,448,364 A | 9/1995 | Moran | 356/430 |
| 5,456,102 A | 10/1995 | Moorehead | 73/3 |
| 5,457,526 A | 10/1995 | Kosaka | 356/72 |
| 5,467,189 A * | 11/1995 | Kreikebaum et al. | 356/336 |
| 5,469,251 A * | 11/1995 | Kosaka et al. | 356/73 |
| 5,481,357 A | 1/1996 | Ahsan et al. | 356/338 |
| 5,506,673 A | 4/1996 | Kosada et al. | 356/72 |
| 5,561,515 A | 10/1996 | Hairston et al. | 356/28 |
| 5,600,438 A | 2/1997 | Kreikebaum et al. | 356/339 |
| 5,646,597 A | 7/1997 | Hamburger et al. | 340/627 |
| 5,684,585 A | 11/1997 | Girvin | 356/336 |
| 5,701,012 A | 12/1997 | Ho | 250/461.2 |
| 5,864,399 A | 1/1999 | Girvin et al. | 356/339 |
| 5,895,922 A | 4/1999 | Ho | 250/491.2 |
| 5,946,093 A | 8/1999 | DeFreez et al. | 356/339 |
| 5,969,622 A | 10/1999 | Hamburger et al. | 340/627 |
| 5,986,555 A | 11/1999 | Hamburger et al. | 340/627 |
| 5,995,686 A | 11/1999 | Hamburger et al. | 385/12 |
| 6,008,729 A | 12/1999 | Hamburger et al. | 340/627 |
| 6,087,947 A | 7/2000 | Hamburger et al. | 340/627 |
| 6,312,914 B1 * | 11/2001 | Kardos et al. | 435/6 |
| 6,386,015 B1 | 5/2002 | Rader et al. | 73/31 |
| 6,819,411 B1 * | 11/2004 | Sharpe et al. | 356/72 |
| 6,831,279 B2 | 12/2004 | Ho | 250/468.1 |
| 6,972,424 B1 * | 12/2005 | Quist et al. | 250/573 |
| 7,053,783 B2 * | 5/2006 | Hamburger et al. | 340/630 |
| 7,106,442 B2 * | 9/2006 | Silcott et al. | 356/338 |
| 2001/0012429 A1 | 8/2001 | Wach et al. | 385/115 |
| 2001/0024800 A1 | 9/2001 | Garcia-Rubio et al. | 435/7.21 |
| 2002/0028519 A1 | 3/2002 | Yguerabide et al. | 436/518 |
| 2002/0032165 A1 | 3/2002 | Johnson et al. | 514/44 |
| 2002/0045276 A1 | 4/2002 | Yguerabide et al. | 436/518 |
| 2002/0046966 A1 | 4/2002 | Muscate-Magnussen | 210/198.2 |
| 2002/0065468 A1 | 5/2002 | Utzinger et al. | 600/476 |
| 2002/0103517 A1 | 8/2002 | West et al. | 607/88 |
| 2002/0119486 A1 | 8/2002 | Oberhardt | 435/6 |
| 2002/0132766 A1 | 9/2002 | DeGrado et al. | 514/12 |
| 2002/0135752 A1 | 9/2002 | Sokolov et al. | 356/39 |
| 2002/0143243 A1 | 10/2002 | Georgakoudi et al. | 600/310 |
| 2002/0165456 A1 | 11/2002 | Canpolat et al. | 600/473 |
| 2002/0171831 A1 | 11/2002 | Backman et al. | 356/369 |
| 2003/0013973 A1 | 1/2003 | Georgakoudi et al. | 600/473 |
| 2003/0022249 A1 | 1/2003 | Schmitz et al. | 435/7.21 |
| 2003/0030783 A1 | 2/2003 | Roche et al. | 356/39 |
| 2003/0052281 A1 | 3/2003 | Rader et al. | 250/461.1 |
| 2003/0077627 A1 | 4/2003 | Worthington et al. | 435/6 |
| 2003/0093092 A1 | 5/2003 | West et al. | 606/139 |
| 2003/0096302 A1 | 5/2003 | Yguerabide et al. | 435/7.1 |
| 2003/0098421 A1 | 5/2003 | Ho | 250/458.1 |
| 2003/0098422 A1 | 5/2003 | Silcott et al. | 250/458.1 |
| 2003/0124733 A1 | 7/2003 | Bushway et al. | 436/174 |
| 2003/0137669 A1 | 7/2003 | Rollins et al. | 356/479 |
| 2003/0139886 A1 | 7/2003 | Bodzin et al. | 702/28 |
| 2003/0157731 A1 | 8/2003 | Yaguerabide et al. | 436/523 |
| 2003/0157732 A1 | 8/2003 | Baker et al. | 436/531 |
| 2003/0159498 A1 | 8/2003 | Small | 73/24.02 |
| 2003/0207328 A1 | 11/2003 | Yguerabide et al. | 435/7.1 |
| 2003/0223063 A1 | 12/2003 | Hill et al. | 356/340 |
| 2003/0228682 A1 | 12/2003 | Lakowicz et al. | 435/287.2 |
| 2003/0231309 A1 | 12/2003 | Fulghum, Jr. et al. | 356/338 |
| 2003/0232445 A1 | 12/2003 | Fulghum, Jr. | 436/63 |
| 2004/0009941 A1 | 1/2004 | Johnson et al. | 514/44 |
| 2004/0021861 A1 | 2/2004 | Lewis et al. | 356/326 |
| 2004/0023317 A1 | 2/2004 | Motamedi et al. | 435/14 |
| 2004/0038413 A1 | 2/2004 | Kramer | 436/63 |
| 2004/0057050 A1 | 3/2004 | Beck et al. | 356/336 |
| 2004/0072356 A1 | 4/2004 | Senisterra et al. | 436/63 |
| 2004/0073120 A1 | 4/2004 | Motz et al. | 600/478 |
| 2004/0079893 A1 | 4/2004 | Dietz et al. | 250/458.1 |
| 2004/0159799 A1 | 8/2004 | Saccomanno | 250/461.1 |
| 2004/0161143 A1 | 8/2004 | Dietz et al. | 382/133 |
| 2004/0174821 A1 | 9/2004 | Eggeling et al. | 370/252 |
| 2004/0197232 A1 | 10/2004 | Kramer | 422/73 |
| 2004/0218184 A1 | 11/2004 | Jorgenson et al. | 356/419 |
| 2005/0019842 A1 | 1/2005 | Prober et al. | 435/7.9 |
| 2005/0020922 A1 | 1/2005 | Frangioni et al. | 600/473 |
| 2005/0020923 A1 | 1/2005 | Frangioni et al. | 600/473 |
| 2005/0026831 A1 | 2/2005 | Bodmer et al. | 514/12 |
| 2005/0057749 A1 | 3/2005 | Dietz et al. | 356/318 |
| 2005/0073683 A1 | 4/2005 | Gard et al. | 356/337 |
| 2005/0079526 A1 | 4/2005 | Senisterra et al. | 435/6 |
| 2005/0112784 A1 | 5/2005 | Yguerabide et al. | 436/518 |
| 2005/0119541 A1 | 6/2005 | Lorenz et al. | 600/316 |
| 2005/0130324 A1 | 6/2005 | West et al. | 436/523 |
| 2005/0137130 A1 | 6/2005 | Bodmer et al. | 514/12 |
| 2005/0141843 A1 | 6/2005 | Warden et al. | 385/141 |
| 2005/0147533 A1 | 7/2005 | Cole et al. | 422/73 |
| 2005/0172852 A1 | 8/2005 | Anderson et al. | 106/31.03 |
| 2005/0194546 A1 | 9/2005 | Saccomanno | 250/461.1 |
| 2005/0220886 A1 | 10/2005 | Bodmer et al. | 424/489 |
| 2005/0240107 A1 | 10/2005 | Alfano et al. | 600/476 |
| 2005/0243307 A1 | 11/2005 | Silcott et al. | 356/73 |
| 2005/0243314 A1 | 11/2005 | Chinnock | 356/364 |

FOREIGN PATENT DOCUMENTS

| | | |
|---|---|---|
| EP | 0 463 795 | 6/1991 |
| EP | 0 618 440 | 3/1994 |
| EP | 0 737 307 | 6/1994 |
| EP | 0 435 166 | 10/1995 |
| EP | 0 711 991 | 5/1996 |
| EP | 0 595 290 | 7/1997 |
| EP | 0 475 748 | 11/1997 |
| EP | 1 158 292 | 11/2001 |
| GB | 1 298 658 | 1/1970 |

| | | |
|---|---|---|
| GB | 2 044 445 | 1/1980 |
| JP | 02-165033 | 6/1990 |
| JP | 03-108635 | 5/1991 |
| JP | 04-185654 | 7/1992 |
| WO | WO 90/10282 | 9/1990 |
| WO | WO 91/10123 | 7/1991 |
| WO | WO 93/16368 | 8/1993 |
| WO | WO 95/09354 | 4/1995 |
| WO | WO 98/34094 | 6/1998 |

OTHER PUBLICATIONS

"Bio-Aerosol Fluorescence Sensor" Jeys et al., Proc. IRIS Active Systems, 1998, vol. 1, p. 235-249.

"Simslin II-A Portable Airborne Dust Measuring Instrument Employing a Light Scattering Technique" Casswell et al., Conference Proceedings of the Fourth WVU Conference on Coal Mine Electrotechnology, 1978, pp. 20-1 to 21-1.

"Instrumentation Airborne Particle Counters-IPS Series" Clean Room Products, Inc., pp. H1-H4.

Met One Model 228 and 229 Particle Concentration Meter and Particle Counter, Date Unknown, prior to 1996.

APC Airborne Particle Counter Model P3610 Article, Bioset, 2002.

* cited by examiner

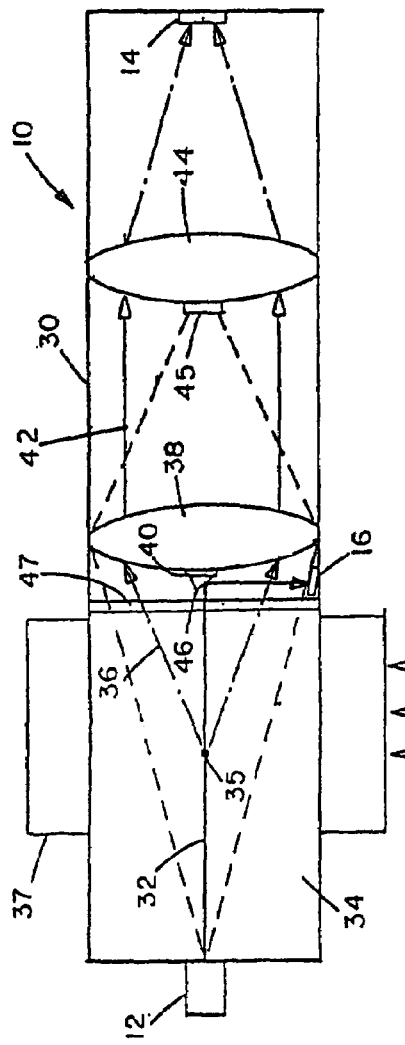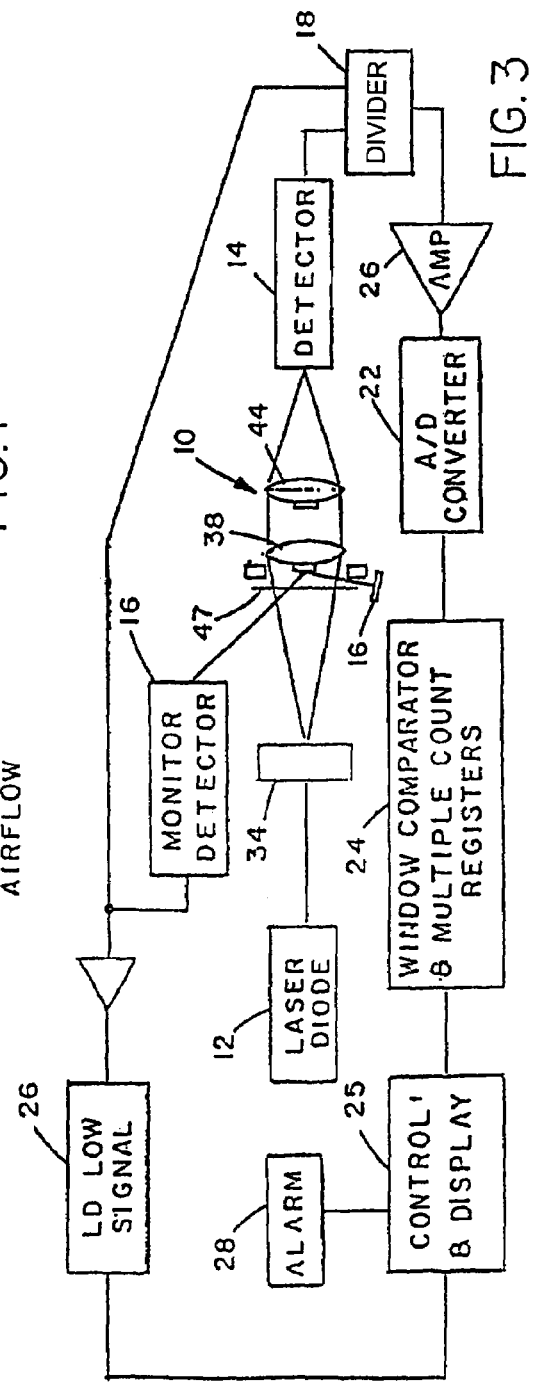

(Hill et al, Field Ana. Chem. & Tech, 3(4-5), 221, 1999)

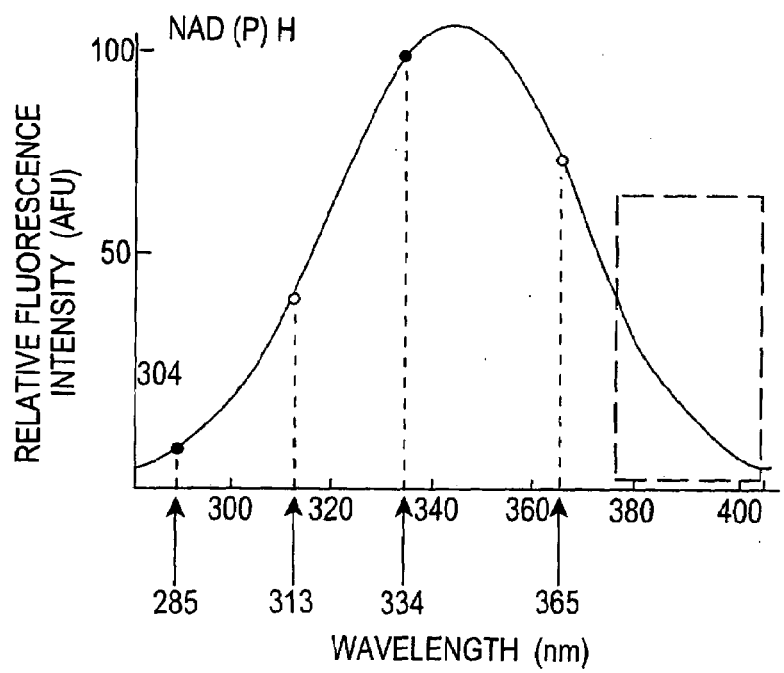
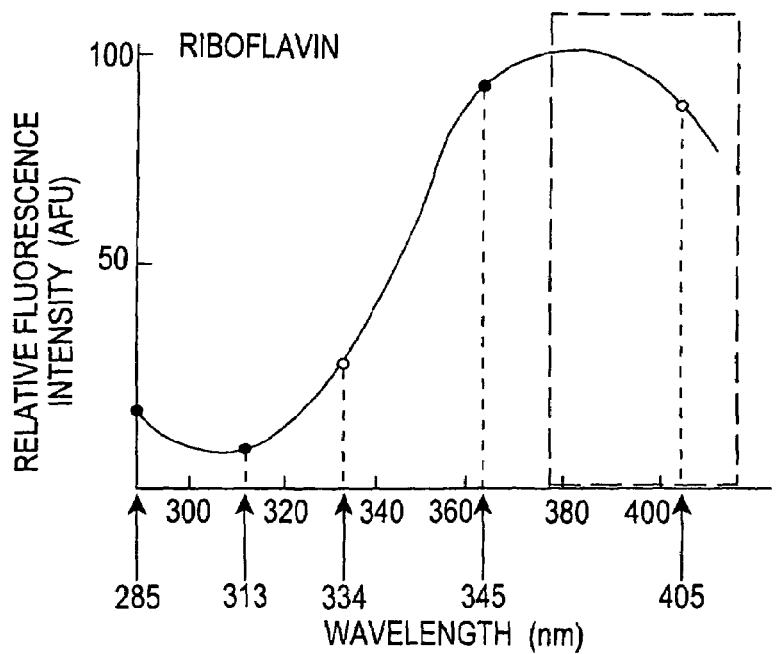

PATHOGEN AND PARTICLE DETECTOR SYSTEM AND METHOD

CROSS REFERENCE TO RELATED APPLICATION

This application claims priority to four U.S. provisional applications: Ser. No. 60/592,618, entitled, "Pathogen Detector System and Method," filed Jul. 30, 2004; Ser. No. 60/592,619, entitled, "Particle Detector System and Method," filed Jul. 30, 2004; Ser. No. 60/606,212, entitled, "Pathogen Detector System and Method," filed Sep. 1, 2004; and Ser. No. 60/683,534, entitled, "Improvements in Pathogen Detector Systems," filed May, 20, 2005. All four U.S. provisional applications are entirely incorporated herein by reference.

FIELD OF THE INVENTION

The present invention relates generally to a system and method for detecting airborne or waterborne particles, and more particularly to a system and method for detecting airborne or waterborne particles and classifying the detected particles by size. The invention has particular utility in detecting and classifying by size allergens and biological warfare agents in fluids, i.e., airborne or waterborne particles, and will be described in connection with such utility, although other utilities are contemplated.

BACKGROUND OF THE INVENTION

An urban terrorist attack involving release of biological warfare agents such as *bacillus anthracis* (anthrax) is presently a realistic concern. Weaponized anthrax spores are extremely dangerous because they can gain passage into the human lungs. A lethal inhalation dose of anthrax spores for humans, $LD_{50}$ (lethal dose sufficient to kill 50% of the persons exposed) is estimated to be 2,500 to 50,000 spores (see T. V. Inglesby, et al., "Anthrax as a Biological Weapon", JAMA, vol. 281, page 1735, 1999). Some other potential weaponized bio-agents are *yersinia pestis* (plague), *clostidium botulinum* (botulism), and *francisella tularensis*. In view of this potential threat, there is currently a need for an early warning system to detect such an attack.

Laser particle counters are known in which a laser beam is directed through a sample and the light, which travels through the sample, is detected and analyzed to detect scattered light from particles in the sample. One problem with existing detectors or particle counters which, are designed for detection of scattered light is that the scattering signal must be extracted from the incident illumination light source signal. This involves detecting a weak signal (scattering from small particles) from a very noisy background (glare from the laser source). Currently, conventionally designed laser particle counters are fragile and expensive, and unsuited to this application. The conventional techniques used for laser particle counting include the laser Doppler method, which measures the speed of the particle and deduces size information, the transient time method which measures the time needed for particles to traverse a sensing region, and large angle multi-sensor design, which is capable of measuring only small particles. A proposed bio-sensor based on laser-induced fluorescence using a pulsed UV laser is described by T. H. Jeys, et al., Proc. IRIS Active Systems, Vol. 1, p. 235, 1998. This is capable of detecting an aerosol concentration of five particles per liter of air, but involves expensive and delicate instruments. See also Hairston et al., J. Aerosol Sci., Vol. 28, No. 3, p. 471-482 (1997). Other particle counters are manufactured by Met One Instrument, Inc, of Grants Pass, Oregon, Particle Measurement Systems, Inc., of Boulder, Colo., and Terra Universal Corp., of Anaheim, Calif. By virtue of their design, these particle counter configurations require precision optical alignment, as well as sophisticated sensors and electronics. These products are geared towards laboratory use and cost thousands of dollars for a single unit. Thus, they are not suitable for a field-deployed detector, nor are they designed specifically for detection of biological warfare agents.

Various detectors have been designed to detect airborne allergen particles and provide warning to sensitive individuals when the number of particles within an air sample exceeds a predetermined minimum value. These are described in U.S. Pat. Nos. 5,646,597, 5,969,622, 5,986,555, 6,008,729, and 6,087,947, all of Hamburger et al. These detectors all involve direction of a light beam through a sample of environmental air such that part of the beam will be scattered by any particles in the air, a beam blocking device for transmitting only light scattered in a predetermined angular range corresponding to the predetermined allergen size range, and a detector for detecting the transmitted light. An alarm is actuated if the light detected at the detector is above a predetermined level. Although these devices are sufficient for the purpose of providing an alarm indication based on the presence of allergen particles, they are not suitable for field deployment and do not meet the more stringent requirements for a pathogen detector for detecting biological warfare agents.

SUMMARY OF THE INVENTION

The present invention provides a new and improved particle/pathogen detector system and method for detecting and classifying airborne or waterborne particles.

According to one aspect of the present invention, a particle detector system is provided, which comprises an outer housing having a sample area for containing sample air or water, a light source for directing a focused beam of light through the sample air, or water whereby portions of the beam of light are scattered at various angles by particles of various sizes present in the sample area, and an unscattered portion of the beam of light remains unscattered, a beam blocking device for blocking at least the unscattered portion of the beam of light and directing at least part of the scattered light along a light path, a detector positioned in the light path after the beam blocking device for detecting light directed by the beam blocking device onto the detector, and producing output pulses in which each pulse has a height proportional to particle size, a pulse height discriminator for obtaining the size distribution of airborne or waterborne particles in the sample at a given time, and an alarm unit for providing a warning signal if the number of particles within a predetermined size range of interest. The beam blocking device will stop the unscattered incident laser beam, efficiently eliminating background noise caused by the light source, and then detecting the angular distribution and intensity of light scattered by particles in an air or water sample, converting the output of the detector into a particle size distribution histogram, and producing an alarm signal if the histogram indicates unusually large numbers of particles within a predetermined size range. The predetermined size range will depend on the particles of interest. For airborne mold, the size range of interest typically is about 1 to 3 µm; for airborne bio-agents the size range of interest typically is about 1 to 7 µm; while for airborne allergens or other harmful substances such as beryllium dust or asbestos the size range of interest typically is about 5 to 50 µm. In the case of waterborne particles of interest, which typically may comprise bacteria or bacterial spores, the size range of interest typically is about 1 to 20 microns.

In an exemplary embodiment of the invention, the output of the pulse height discriminator is connected to a processing unit for processing the particle size distribution at a given time, based on the height of each pulse, producing a histogram of the airborne or waterborne particle size distribution, and displaying the histogram on an output device. The discriminator may comprise a peak detector for measuring incoming pulse height, and a comparator and register for registering the number of pulses in each pulse height. The respective pulse heights are then converted into particle sizes, and a histogram of the particle size distribution is displayed on a suitable display unit, such as an LED or liquid crystal display, or a computer screen.

An alarm device may also be provided to produce an audible and/or visible alarm signal if the number of pulses in a certain particle size range exceeds a predetermined normal background value. For example, in the case where bio-agents are of interest any sudden and localized increase in the number of airborne particle counts in the size range from 1 µm to 7 µm would normally signify an intentional release of hostile bio-agents.

In an exemplary embodiment of the invention, a reflector is placed on or in front of the beam blocker in order to reflect part of the unscattered portion of the incident light beam, and a second photodetector is positioned to detect light reflected from the reflector. The function of the photodetector is to monitor the output of the light source, which may be a laser diode. This allows for self-calibration of the apparatus. The particle size measurement relies on the electrical pulse height measurement, and it is therefore important to account for any fluctuations in the laser diode power output. The electrical pulse signal from the first detector may be divided by the monitoring signal from the second detector in order to ensure that the results are not affected by any laser power variations. The output of the second photodetector is also monitored to indicate the laser diode performance. When the signal from the second photodetector falls below a predetermined level, such as 50% of the starting power level, a "Laser Power Low" alarm will sound, in order to initiate a maintenance call.

A transparent partition slide may be provided between the sample area and the beam blocking device. The purpose of the slide is to prevent dust or other environmental pollutants from reaching the optical elements and photodetectors. This will be particularly beneficial when the system is used in harsh field deployment conditions. The slide is replaced when it becomes too dirty to allow sufficient light transmission, which will be determined by the second photodetector. Thus, the laser power alarm may indicate either that the laser diode has lost power, or that the slide has become too dirty. A moderately dirty partition slide will not affect the accuracy of particle detection, since it will reduce the light intensity of both the unscattered portion of the light beam and the scattered light beam, and the ratio of these two signals is recorded.

According to another aspect of the present invention, a method of detecting and classifying by size airborne or waterborne particles is provided, which comprises the steps of:

directing a light beam through a sample of air or water such that a first portion of the light beam is scattered by particles present in the sample and a second portion remains unscattered;

receiving both portions of the light beam, which have passed through the sample, and directing the light beam portions onto a beam blocking device;

blocking at least the second portion of the light beam at the beam blocking device and direction at least part of the first portion of the light beam onto a first detector;

measuring the pulse height of electrical pulses output from the first detector;

counting the number of pulses of each pulse height in a predetermined time interval;

converting the pulse heights to particle sizes;

counting number of pulses corresponding to each particle size; and producing an alarm signal if the number of pulses detected within a predetermined size range is exceeded.

In an exemplary embodiment of the invention, the data regarding number of pulses for each particle size is converted into a histogram of the detected particle size distribution. This may then be compared to known bio-agent particle size distributions, and an alarm may be activated if the detected distribution matches any known bio-agent particle size distribution. The size distribution may also be used to identify the particular bio-agent detected, and may provide a forensic tool for identifying the manufacturing process by which the weaponized bio-agent was produced.

The particle detection system and method of this invention can be used to detect the presence of airborne or waterborne biological warfare agents or other harmful substances including mold, bacterial, bacterial spores, and dusts such as beryllium and asbestos.

In another embodiment of the invention there is provided an improved detection system and method which can be used to both detect the presence of airborne or waterborne particles within a selected size range and also differentiate between biological organisms or biological agents and inert or inorganic substances within that selected size range. More particularly, the present invention provides an airborne or waterborne particle detector in combination with a fluorescence sensor for detecting and discriminating between airborne or waterborne particles of living organisms or bio-agents from inert substances. The system of the present invention detects particles of a given size range of interest, e.g., about 1 to about 7 microns, and differentiates between biological organisms or biological agents and inert or inorganic substances within that size range.

In another aspect, the present invention provides an improved detection system and method which can be used to both detect the presence of airborne or waterborne particles within a selected size range and also to differentiate between biological organisms or biological agents and inert or inorganic substances within that selected size range.

Another embodiment of the present invention provides an improved fluorescence detector and method by utilizing multiple detection housings. More specifically, a passageway in which a fluid containing biological organisms or biological agents can flow is used to connect a series of housings. Each housing contains a light source for sending light through the fluid and a detector positioned in the light path for detecting the fluorescence and particle size of the biological organisms or biological agents and producing a corresponding output signal. Preferably, the light source is tuned to produce light of an optimal excitation wavelength of one or more metabolites. For example, the light source may be tuned to the excitation wavelength of tryptophan, pyridoxine, NADH, or riboflavin. Furthermore, the housing may contain multiple light sources with one light source in each housing having a common wavelength to ensure consistent particle size measurements.

In another exemplary embodiment of the invention, a particle/fluorescence detector system uses a plurality of light sources for sending light beams through a fluid to excite fluorescence of said biological organisms or biological agents in the fluid. The plurality of light sources are mixed using an optical coupler or another mixing device. Preferably, the optical coupler modulates the plurality of light beams at different frequencies. A detector is positioned in the light path for detecting the fluorescence and particle size of said biological organisms or biological agents and producing a corresponding output signal.

In yet another exemplary embodiment of the invention, a reflection mechanism is placed in the path of light after the light has passed through a sample area containing fluid. The reflection mechanism deflects into a second light path at least a portion of the light scattered at a certain range of angles. A first detector is placed in the second light path for detecting a portion of the scattered light and producing an output signal. The first detector is preferable optimized for measuring particles a first size range, e.g., from 0.1 µm to 1.0 µm in size. A second detector is positioned in the light path after the reflecting mechanism for detecting a portion of the light scattered at larger angles and producing a corresponding output signal. The second detector is preferable optimized for measuring particles of a second size range, e.g., from 1 µm to 10 µm in size.

Furthermore, in this embodiment, a wavelength selective filter or beam splitting mechanism may be placed in said light beam after the reflection mechanism to split the beam into a plurality of light beams. In a preferred embodiment, the wavelength selective filter is a dichroic filter. A third detector may be placed in the light path of one of the plurality of beams for detecting the fluorescence of particles in the sample area.

In another embodiment of the invention involves a test mechanism for the testing system for a particle detection sensor including
a chamber for loading a test powder;
a filter mechanism for removing particles above predetermined size connected to said chamber;
an exit of said filter is connected to a particle detection sensor system.

This detector system is sensitive, inexpensive, and rugged enough for field deployment. Although the system does not necessarily always detect or identify an exact particle, it can provide a sensitive and cost effective early warning of a bio-agent attack. It also can be arranged to provide early warning of harmful airborne particles, which may case pulmonary distress, such as asbestos and beryllium dusts, or harmful waterborne particles.

BRIEF DESCRIPTION OF THE DRAWINGS

The present invention will be better understood from the following detailed description of an exemplary embodiment of the invention, taken in conjunction with the accompanying drawings in which like reference numerals refer to like parts and in which:

FIG. 1 is a schematic block diagram of the optical portion of a particle detector system according to an exemplary embodiment of the invention;

FIG. 3 is a block diagram of the particle detector system according to an exemplary embodiment of the invention, incorporating the optical system of FIG. 1;

FIG. 21 is a graph of the fluorescence emission as a function of wavelength for NADPH;

FIG. 22 is a graph of the fluorescence emission as a function of wavelength for riboflavin;

DETAILED DESCRIPTION OF THE DRAWINGS

Figure 6:
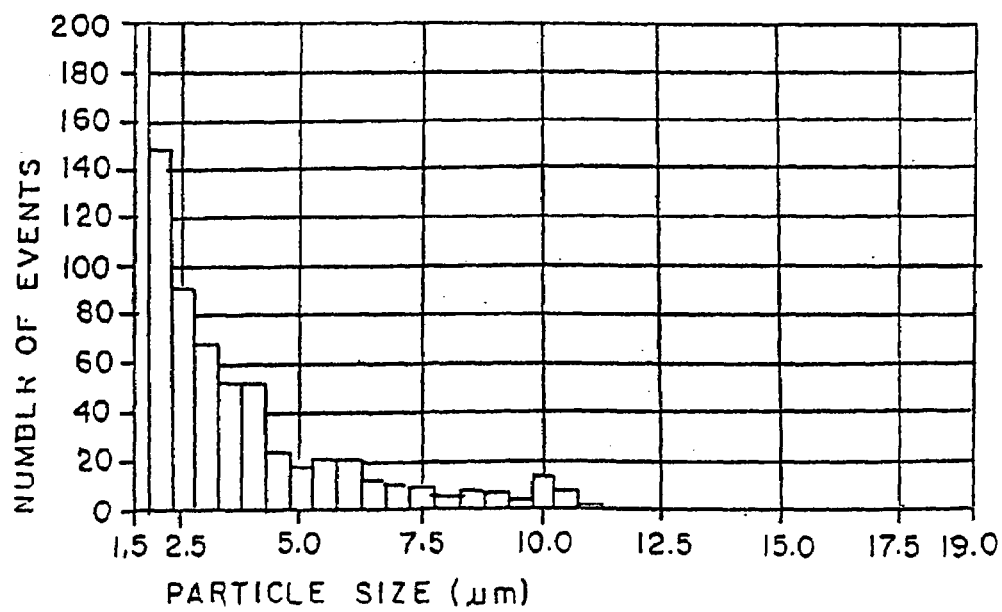
FIG. 6 illustrates an exemplary output histogram displayed by the system of FIGS. 3 and 4 in a situation where particle counts within a predetermined size exceed a predetermined amount, triggering an alarm condition.

FIGS. 1, 1A and 3 to 5 illustrate an airborne particle detector system according to an exemplary embodiment of the invention, while FIG. 6 illustrates an exemplary output from the system. This embodiment of the system is particularly intended to detect airborne or waterborne bio-terrorist agents deliberately released by terrorists or others, but may also be used in civilian applications to detect harmful levels of other airborne or waterborne particles which may exist naturally such as mold or bacteria, or which may have been accidentally, inadvertently, naturally, or deliberately released.

The term "fluid borne particles" as used herein means both airborne particles and waterborne particles.

The term "collimated light" as used herein means both collimated light and near collimated light.

The term "pathogen" as used herein refers to any airborne or waterborne particles, biological agent, or toxin which could potentially harm or even kill humans exposed to such particles if present in the air or water in sufficient quantities. As used herein, "biological agent" is defined as any microorganism, pathogen, or infectious substance, toxin, biological toxin, or any naturally occurring, bioengineered or synthesized component of any such micro-organism, pathogen or infectious substance, whatever its origin or method of production. Such biological agents include, for example, biological toxins, bacteria, viruses, rickettsiae, spores, fungi, and protozoa, as well as others known in the art.

"Biological toxins" are poisonous substances produced or derived from living plants, animals, or microorganisms, but also can be produced or altered by chemical means. A toxin, however, generally develops naturally in a host organism (i.e., saxitoxin is produced by marine algae), but genetically altered and/or synthetically manufactured toxins have been produced in a laboratory environment. Compared with microorganisms, toxins have a relatively simple biochemical composition and are not able to reproduce themselves. In many aspects, they are comparable to chemical agents. Such biological toxins are, for example, botulinum and tetanus toxins, staphylococcal enterotoxin B, tricothecene mycotoxins, ricin, saxitoxin, Shiga and Shiga-like toxins, dendrotoxins, erabutoxin b, as well as other known toxins.

The detector system is designed to detect airborne or waterborne particles within a specific size range, discriminate between biologic agents and inert or inorganic materials, and produce outputs indicating the number of particles of each size within the range which is detected in a sample and indicate whether the particles are biologic or non-biologic, and also to produce an alarm signal if the number of particles exceeds a predetermined value above a normal background level, and/or are biological organisms or biological agents and potentially dangerous.

As illustrated in FIGS. 1 and 3, the first embodiment of the system basically comprises an optical unit 10, a laser diode or other light source 12 directing a collimated or nearly collimated light beam into the optical unit 10, a first photodetector 14 at the output of optical unit detecting light transmitted through the unit, a second photodetector 16 for detecting the light output of the laser diode, a signal divider 18 for dividing the output of photodetector 14 by the output of photodetector 16, an amplifier 26 connected to the output of differential amplifier 18, an analog to digital converter 22, a window comparator circuit 24, and a control and output display unit 25 connected to the output of circuit 24. A low signal detection circuit 26 is connected to the output of photodetector/monitor detector 16 which detects the laser diode power, and the output of circuit is also connected to control unit 25. An alarm device 28 is also connected to control unit 25. Control unit 25 can be a computer or custom designed hardware/software to control the system.

The optical portion 10 of the system will now be described in more detail with reference to FIGS. 1 and 1A. A portion of this system is similar to the optical system described in U.S. Pat. Nos. 5,986,555 and 6,087,947 of Hamburger et al., the contents of which are incorporated herein by reference. The optical system will be contained in an outer housing 30, which may be of tubular or other shapes. The light source 12 directs a collimated laser light beam 32 through an air sample region 34 within the housing. When the collimated light beam 32 strikes particles 35 within the air sample, a portion of the beam 36 is deflected or scattered, with the angle of deflection being dependent on the size of the particle. Scattered portions 36 of the light beam therefore establish the presence of particles within the sample. Environmental air is constantly drawn through the sample region 34 in the direction of the arrows in FIG. 1 by a fluid moving unit 37 such as a fan, in the same way as described in the patents referenced above.

Figure 1A:
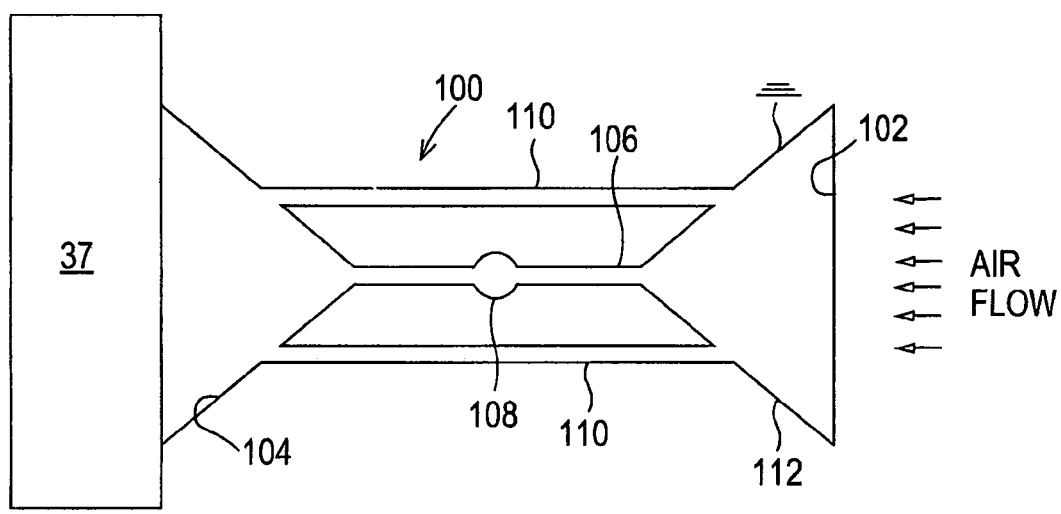
FIG. 1A shows details of the sample region portion of the detector system of FIG. 1.

Referring to FIG. 1A, in order to ensure accurate particle detection the flow channel through the sample region 34 should be relatively small, preferably about 1 to 2 mm across. Making the flow channel too small in cross section, i.e., below about 1 mm, creates too much back pressure for accurate sampling. On the other hand, a flow channel in excess of about 2 mm may result in a double layer or still layer adjacent the flow channel walls. Ideally, the flow channel will have a cross-section of about 1.5 to about 2.0 mm. In a preferred embodiment, the sample region 34 comprises a flow cell 100 comprising a body having an inlet end 102 and an outlet end 104. The inlet end 102 and the outlet end 104 each take the form of truncated cones which may be the same or different shapes. A channel 106 of about 1 to about 2 mm in cross section includes an optical window 108 through which light beam 32 is directed. Channel 106 connects the inlet end 102 and outlet end 104 at the apexes of the truncated cones. Inlet 102 is open to the ambient air. Fluid moving unit 37, e.g. a fan, is connected at outlet 104. In order to reduce back flow pressure one or more additional conduits 110 preferably are formed between the midpoint of the inlet end cone conical surface and the outlet end cone surface to bleed air and thereby permit more uniform air fluid sampling. Preferably, the outside surface of the flow cell 100 is coated with a metalized coating 112 which is connected to ground, in order to obviate potential electrostatic build up.

A lens 38 is located in the housing in the path of both the unscattered and scattered portions of the light beam exiting the sample area. The lens 38 has a central, blocking member 40 of predetermined diameter, which is designed to absorb light. In a first exemplary embodiment, blocking member 40 comprises a black piece of vinyl adhered to the front of lens 38, although other beam diverting devices may alternatively be used. The diameter of the blocking member 40 is such that at least the unscattered portion of the focused light beam is blocked and prevented from traveling any further through unit 10. The diameter of circular blocking member 40 may be about 2 mm greater than the diameter of the unfocused light beam, and may be designed such that it blocks unscattered light and light scattered by particles larger than a predetermined size, such as 50 microns. An even larger blocking member may be used to further eliminate light scattered by particles smaller than 50 microns, if desired. The lens may also have an annular ring (not illustrated) of light blocking material surrounding the central blocking member 40 as described, for example, in U.S. Pat. No. 6,087,947 referred to above. This will act to block light scattered by particles smaller than a predetermined minimum value. However, the lens and housing diameter may alternatively be designed such that light scattered by such particles will not be transmitted.

In the prior patents discussed above, the beam blocking device comprising the lens 38 and beam blocking member 40 (and annular beam blocking ring if present) was designed to block transmission of light scattered by particles outside a predetermined particle size range of 5 to 50 microns. However, in the present invention, the particles of interest may have a different size range, specifically airborne mold, biological agents, or harmful dusts. Since the particles may be as small as 1 µm or even 0.5 µm in size, the lens 38, housing 30, and beam blocking member 40 are of predetermined dimensions such that light transmitted by particles outside a size range of 0.5 µm to 50 µm will be blocked, while portions 42 of the light beam scattered by particles within the size range of 0.5 µm to 50 µm are transmitted through the annular ring portion of the lens which surrounds blocking member 40. It will be understood that the dimensions of the blocking member may be varied if desired to further limit or expand the portion of the light beam transmitted through lens 38.

Light source 12, in addition to the focused light beam 32, also generates a certain amount of noise from its surface. Such noise is focused by lens 38 onto a circular blocking member 45 at the center of the second lens 44, such that it is blocked from reaching the detector 14. However, the scattered portions 42 of the light beam transmitted by lens 38 are focused by lens 44 onto detector 14 as indicated in FIG. 1. Circular blocking member 45 may be identical to blocking member 40.

Beyond the previous discussed differences, optical unit 10 differs from the optical units described in the aforementioned two patents in the following respects. First, a reflector 46 is placed on or in front of the beam blocking member 40. The reflector may be a tilted mirror or a coated prism set. This reflector is designed to reflect the unscattered, incident laser beam onto the second, or monitoring photodetector 16. Secondly, a transparent partition slide 47 is placed between the sample area 34 and the beam blocking device 38, 40. The purpose of the slide is to prevent dust or other environmental pollutants from reaching the optical elements and photodetectors. This will be particularly beneficial when the system is used in harsh field deployment conditions. The slide is removably mounted in the housing so that it can be replaced when it becomes too dirty to allow sufficient light transmission, which will be determined by the second photodetector. Thus, the laser power alarm may indicate either that the laser diode has lost power, or that the slide has become too dirty. A moderately dirty partition slide will not affect the accuracy of particle detection, since it will reduce the light intensity of both the unscattered portion of the light beam and the scattered light beam, and the ratio of these two signals is recorded.

Although the beam diverting device in the illustrated embodiment is a lens having a central blocking region and optionally also an outer blocking ring, such that only light scattered in a predetermined angular region is transmitted to the lens, the blocking device in alternative embodiments may be a concave mirror having a central light absorbing light blocker as above, or a central opening of predetermined diameter. The detector 14 in this case will be positioned to detect light reflected from the concave mirror, as described in U.S. Pat. No. 6,008,729 of Hamburger et al., the contents of which are also incorporated herein by reference. An angled mirror or prism also may be used in exactly the same way as illustrated in FIG. 1 in order to direct part of the unscattered portion of the beam onto the second detector.

Figure 2:
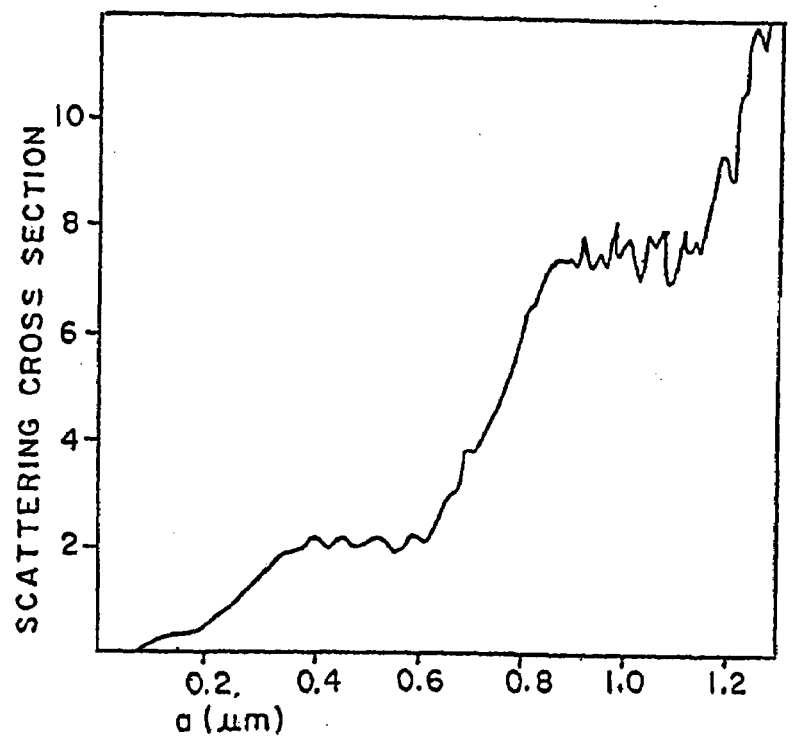
FIG. 2 is a graph illustrating the relationship of Mie scattering cross-section of incident light to the airborne particle size.

The system design is based upon the principle of Mie scattering of light by particles with sizes comparable with the wavelength of light. In the Mie scattering regime, both the angular distribution and the intensity of the scattered light are strongly dependent on particle size and shape. Mie scattering is characterized by the following properties: 1) the scattered light is concentrated in the forward direction; 2) the angular distribution of the scattered light intensity is highly sensitive to the scattering particle size; and 3) the scattering cross-section of a particle is proportional to the particle size in a monotonic but complex manner. Using visible light, such as a visible laser diode light output beam of wavelength 0.67 µm, the Mie scattering method is ideally suited for detecting and characterizing airborne particles in the micron size range. The relationship of Mie scattering cross-section to particle radius is shown in FIG. 2.

The optical unit 10 of the system uses the principle that scattering angle is proportional to particle size in order to eliminate light scattered outside a predetermined range using a beam blocking device 36 positioned in the path of light which has traveled through the sample. The remainder of the system is designed to detect the particle size distribution in the sample by discriminating between pulses of different heights detected at detector 14, since the scattering cross section of a particle is proportional to the particle size in a monotonic but complex manner, as described above and illustrated in FIG. 2. Therefore, the heights of the electrical pulses output from detector 14 are dependent on the particle size.

Figure 4:
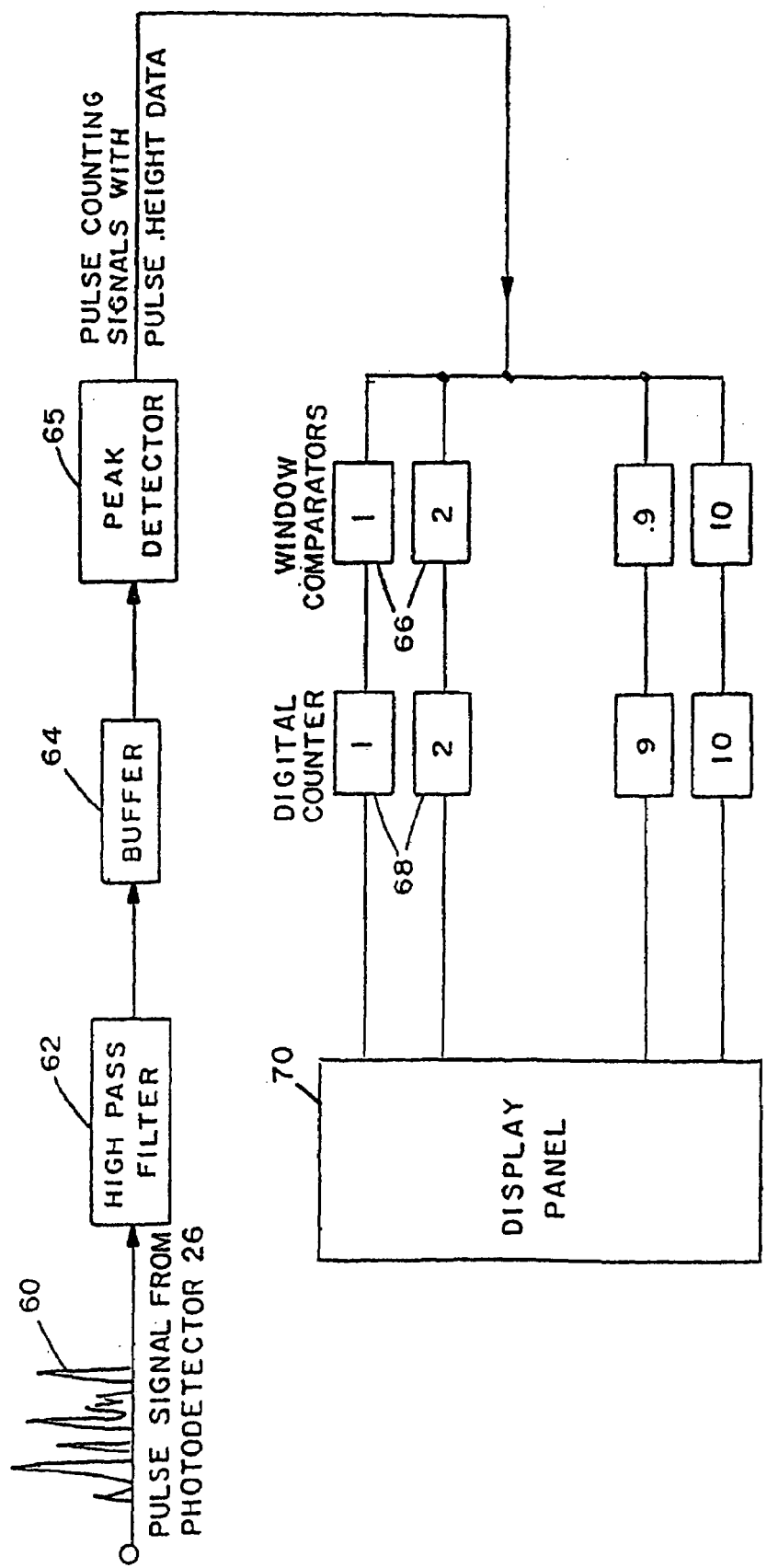
FIG. 4 is a block diagram of a pulse height measurement and display circuit.
Figures 5, 5A:
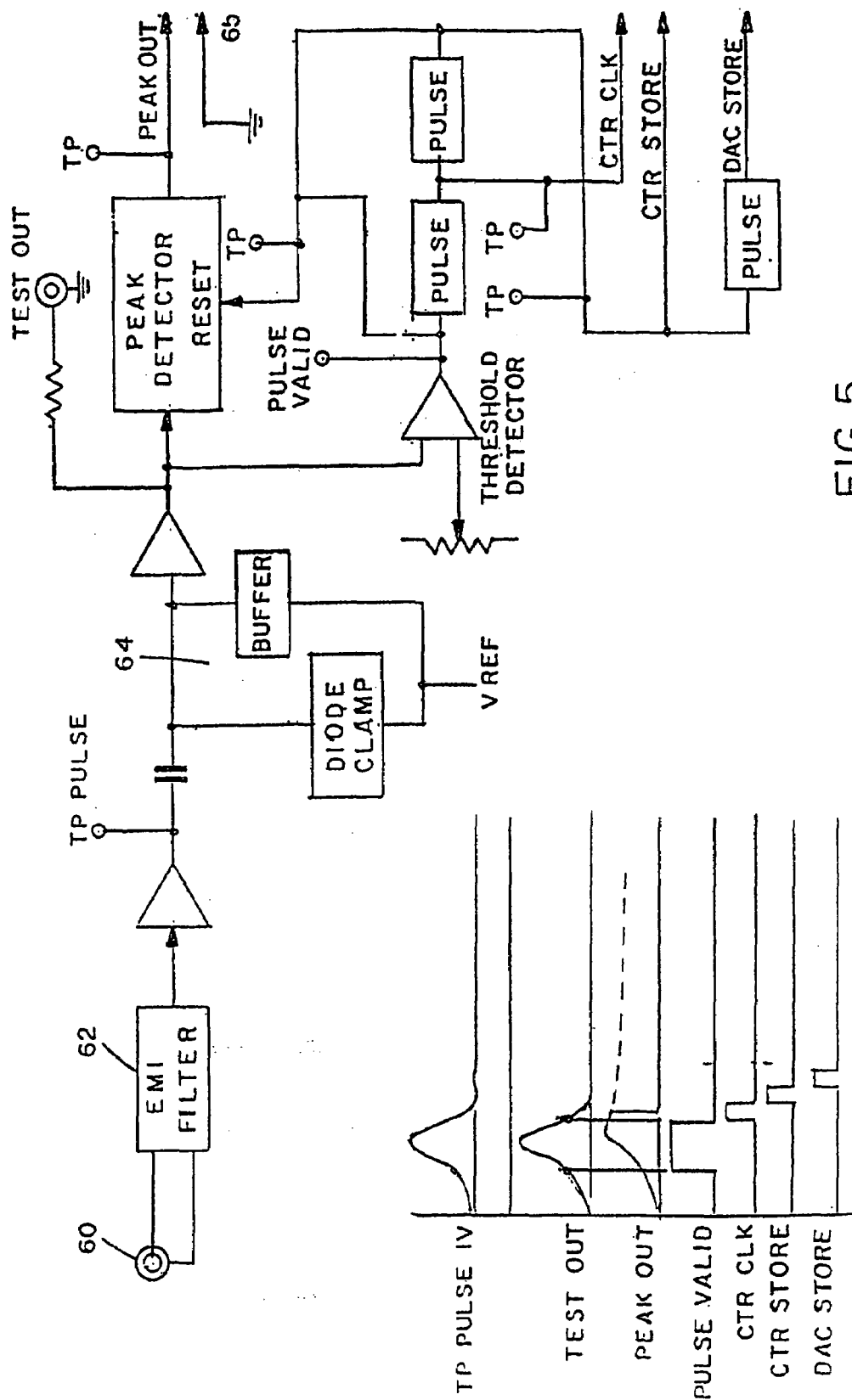
FIG. 5 is a schematic diagram of the analog to digital converter portion of the circuit of FIG. 4.
FIG. 5A is a diagram illustrating pulse wave forms at various points in the circuit.

The output of detector 14 is connected to one input of signal divider 18, as indicated in FIG. 3, while the output of detector 16 (which corresponds to the laser diode output) is connected to the other input of the signal divider 18 and the ratio of these signals is output from the signal divider 18. FIG. 4 is a block diagram of the pulse height measurement circuit, making up the converter unit 22, the window comparator unit 24, and the control and output display unit 25 in an exemplary embodiment of the invention, while FIG. 5 is a schematic illustrating the digital converter unit in more detail. The output of the photodetector will be a pulse signal, for example a signal 60 as illustrated in FIG. 4, of a series of analog pulses, with each pulse representing right scattered by a particle in the air sample, and the height of the pulse being proportional to the particle size. Each incoming pulse from the photodetector passes a high pass filter 62 in order to eliminate the DC background, and then goes through a buffer 64 to a peak detector 65 which will measure the height of the incoming pulse. The output of peak detector 65 will be a series of pulse counting signals with pulse height data. One example of a suitable analog to digital converter and peak detector circuit is illustrated in more detail in FIG. 5, with FIG. 5A illustrating pulse outputs at various points in the circuit. The output signal "PEAK OUT" in FIG. 5A is sent to the window comparator unit for classification. The other pulses illustrated in FIG. 5A are timing and enabling signals to tell the window comparator to take and store the count.

The window comparator unit has a series of window comparators 66 (labeled 1-10 in FIG. 4 by way of example) each designed to detect pulses in a predetermined voltage range (window voltage). Each window comparator 66 will send a signal to its associated digital counter 68 only if the incoming pulse height is within its window voltage (e.g. 5 mV to 7.5 mV for comparator #5). The outputs of the counters 68 are connected to a display panel 70, which will display particle numbers in each particle size, bin. Thus, the output display unit 25 may comprise a bar graph lit by light emitting diode (LED) arrays, with the LEDs being lit up in sequence for each particle size based on input from the associated counter, to produce a histogram of the particle size distribution. The bar graph may be in different colors for the different particle sizes. The outputs may also, or alternatively, be connected to a computer programmed to display a histogram of the particle size distribution on its display screen.

The window comparator unit 24 has a plurality of comparators 66 and counters or bins 68 for counting pulses corresponding to particle sizes in the range of interest. In FIG. 4, ten such bins are shown. However, fourteen bins may be provided for particle sizes from one to seven microns, at a 0.5 micron spacing. A smaller or greater number of comparators and counters may be provided if a smaller or larger size range is required, for example a more limited pathogen size range of 1 to 5 μm. FIG. 6 illustrates an example of a histogram of particle size distribution. Although this indicates a distribution in the range from 1 to 19 μm, it will be understood that the control unit may be programmed to display a particle size distribution histogram over the smaller range of 1-7 cm as discussed above or any desired range. The output of control unit 25 may also be connected to a visible and/or audible alarm device 28, such as an alarm light on the front of the housing and a buzzer or the like.

Any suitable software may be used to generate the output display histogram, such as LabView software available from National Instruments Corporation of Austin, Tex. This software may also be used to produce an output to activate an audible alarm 28 if the number of counts in a size range corresponding to a pathogen or bio-agent particle size exceeds a predetermined level above the normal ambient level. This will help to reduce or even eliminate false alarms. The output of the computer may also be used to trigger a more elaborate bio-agent detection device, such as a PCR based anthrax detection apparatus. This combination detection scheme will be cost effective and will further reduce the risk of a false alarm.

In a modified arrangement of the invention, the histogram of the airborne particle size distribution may be compared to that of known weaponized bio-agents, since the processing procedure for such agents is known to have a signature size distribution unique to the machinery used in the process. Thus, the detector system of this invention can provide forensic information on the possible origin of the bio-agent manufacturer.

As noted above, the most probable bio-agents for use in a terrorist attack have size ranges from 1 μm to 7 μm. Table 1 below shows the characteristics of Category A bio-terrorist agents, as specified by the Center for Disease Control:

TABLE 1

Category A bio-terrorist agent

| AGENT | SIZE CHARACTERISTICS |
|---|---|
| Bacillus Anthracis | Rod shape: width 1.0-1.2 μm, length 3.0-5.0 μm (spore 1.0 × 1.5 μm) |
| Yersinia pestis (plague) | Oval 1.0-2.0 μm |
| Clostidium botulinum | Rod shape: width 0.8-1.3 μm, length 4.4-8.6 μm |
| Francisella tularensis | Rod shape: width 0.2 μm, length 0.7 μm |

There exists in environmental air only a very small and constant concentration of naturally occurring airborne particles in the size range of about 1 μm to 7 μm. The particle size ranges of smog incursion in metropolitan areas and sudden growth of local dust source are peaked at 0.3 μm and 5 μm, respectively. Pollens and other allergens can also be present in the air during blooming seasons, and the size range of allergen particulates is from about 5 to 50 μm. Thus, few of these naturally occurring airborne particles are in the typical size range of weaponized bio-agents (1 to 7 μm). In addition, while mold may have a particle size of about 1 to 5 μm, the amount of mold particles in the air in any particular location generally does not vary suddenly. The detector system of this invention is therefore designed to detect particles in this specific size range and produce an output representing the range of particle sizes detected at 0.5 μm intervals. Any sudden and localized increase in the number of airborne particles within a 1 to 7 μm size range most likely signifies an intentional release of hostile bio-agents or pathogens. The system can be set up to detect and store a natural background level of particles within the size range of interest, and then use this as a comparison level for subsequent output histograms, in order to activate the alarm on detection of a sudden increase. The particle size distribution histogram of FIG. 6 indicates a probable hazardous situation where the number of particles detected in the size range of 1 to 7 μm is way over normal levels.

Although the particle detector system as above described will not identify the particular particle, it will serve as a sensitive and cost-effective warning of an airborne bio-agent attack because of the relative scarcity of airborne particles in the range of interest in normal meteorological conditions. Particles within this range can penetrate the human lungs and could be potentially harmful or even fatal for those inhaling them. The alarm provides a warning for individuals in the vicinity to evacuate the area immediately, reducing the exposure to such agents.

The same detection system and method can also be used to detect hazardous levels of potentially harmful dusts in manufacturing facilities. For example, harmful asbestos fibers are in the size range of about 5 μm, having a typical length of about 5 μm or longer and a diameter of about 1-2 μm. Beryllium dusts are also, harmful when breathed into the lungs, which will happen if they are in the 1-5 μm range. The detection system of this invention could be provided in buildings containing asbestos, or when workers are working in such buildings, to provide a warning signal when an unusual spike in the 1 to 5 μm range is detected, which may indicate harmful levels of asbestos fibers in the air. Similarly, the detector may be used in the vicinity when workers are machining beryllium parts, in order to give a warning signal if the number of particles in the 1 to 5 μm size range suddenly increases, indicating the possible presence of harmful levels of beryllium dust. Even though the detector cannot differentiate asbestos or beryllium dusts from non-harmful particles in the same size range, any sudden increase in detected particle levels in this size range when working with asbestos or beryllium will provide an indication of a potentially hazardous situation requiring evacuation of the area and further testing.

In the detector system described above, a two stage detection and discrimination process is used, with the optical portion 10 of the system first eliminating light scattered outside a predetermined angular range incorporating the particle size range of interest. Subsequently, detected output pulses are discriminated according to pulse height, the number of pulses of each height are counted and converted to particle size within, e.g., 0.2 μm, and the results are displayed as a histogram, with a new histogram being generated at suitable time intervals to illustrate changing particle distribution conditions. However, instead of displaying a particle size distribution histogram, the optical portion of the detector apparatus may alternatively be arranged to direct only that part of the scattered light signal corresponding to a particle size range of 1 to 7 μm to the detector 14, and the remainder of the system is then arranged to emit an alarm signal if the output of the detector exceeds a predetermined threshold level. This will provide a less accurate output, and does not provide any discrimination of particle sizes within the detected size range, but can still give a relatively accurate warning of the presence of an unusually large number of particles within a size range corresponding to known airborne pathogens allergens or other harmful particles, e.g., beryllium dust or asbestos. The optical assembly 10 of FIG. 1 would only have to be modified to provide a larger central blocking area to block light scattered by particles having a size greater than about 7 μm, and the output circuitry would be modified to provide a threshold level discriminator at the output of the detector, and to provide an output signal from the discriminator to activate an alarm if the detected signal is above the selected threshold.

The pathogen detector of this invention can be used in various applications. For example, it may be implemented as a battery powered, portable, hand-held detector for field personnel. In such case, an outer housing may hold both the optical unit as well as the electrical circuitry to count particles by size range, and will have a display of the current particle counts for each particle size, such as an LED display. It also may incorporate a transmitter for sending radio signals to a base station. It may also incorporate an audible alarm and a warning light for laser low power condition. A stand-alone, desk top version may also be provided for use in office buildings or the like. This will be similar to the field version, but will be powered from a standard electrical wall socket via an AC/DC converter. In the latter case, the detector may be used to provide protection from bio-agent contaminated letters or packages in office desk top settings.

Figure 10:
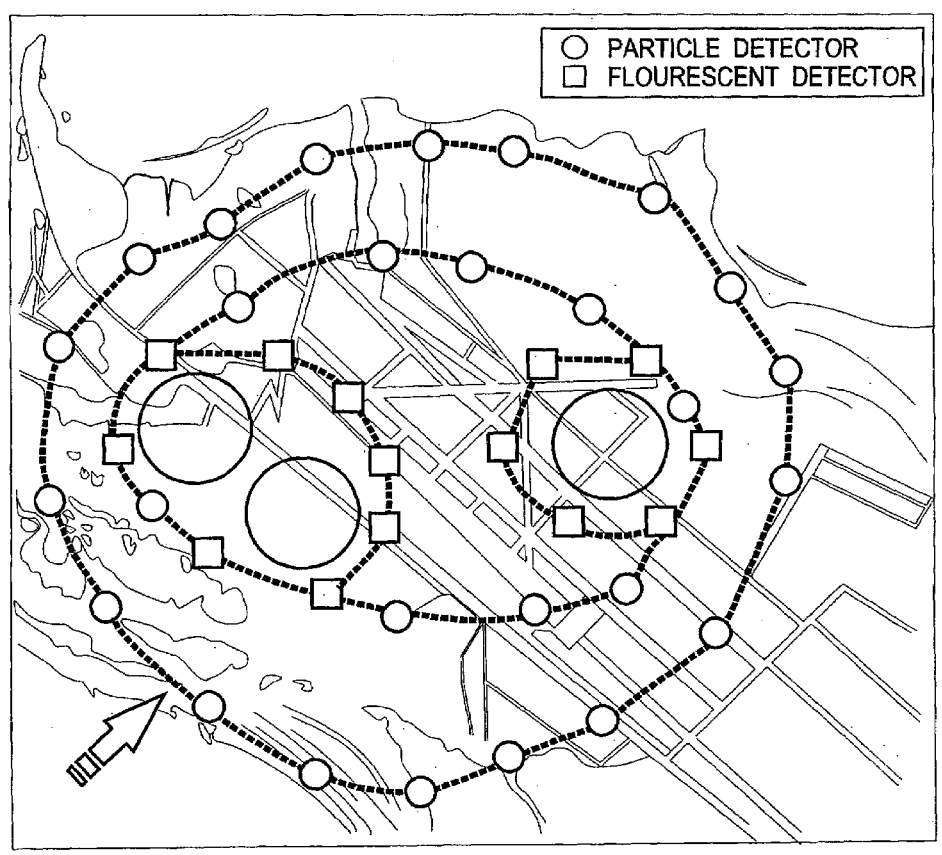
FIG. 10 is a plan view illustrating a plurality of detectors of the present invention in a grid.

The detector also may be part of a multiplexed system for building security, comprising a number of detectors in different rooms linked to a central monitoring computer or control station. The control station can be programmed to monitor the particle counts from each room, and to analyze the origin of any unusual increase in pathogen-size particles, and to predict the potential spread pattern within the building. Larger grid systems may be used in large building complexes, such as military bases or city blocks, i.e., as illustrated in FIG. 10. The detectors may be hard wired, or may have radio transmitters for transmitting data to a central control station which again can analyze the origin of any detected increase in potential bio-agent particles, and the potentially spread of any bio-agent plume.

The airborne particle detector of the present invention also advantageously may be used to monitor clean room facilities for potential contamination and/or material loss.

Figure 7:
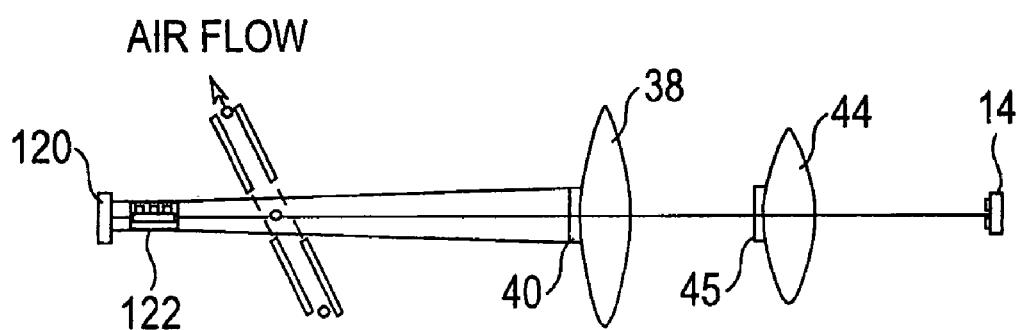
FIGS. 7 and 7A are views similar to FIG. 1 of alternative forms of particle detectors according to the present invention in which an UV LED is employed in place of the laser light source.
Figure 7A:
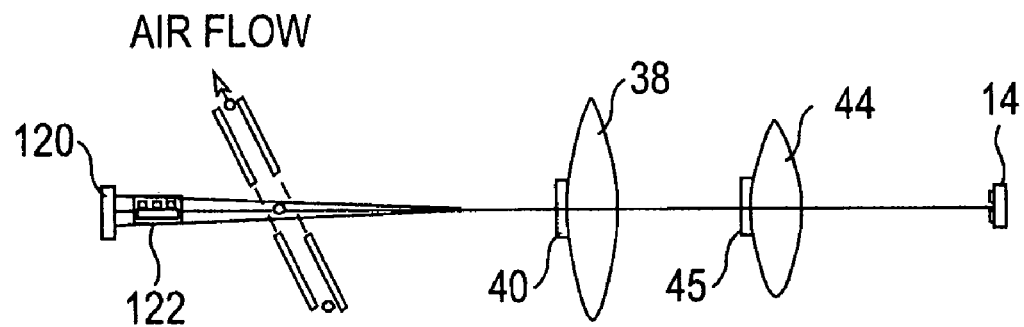
Figure 9:
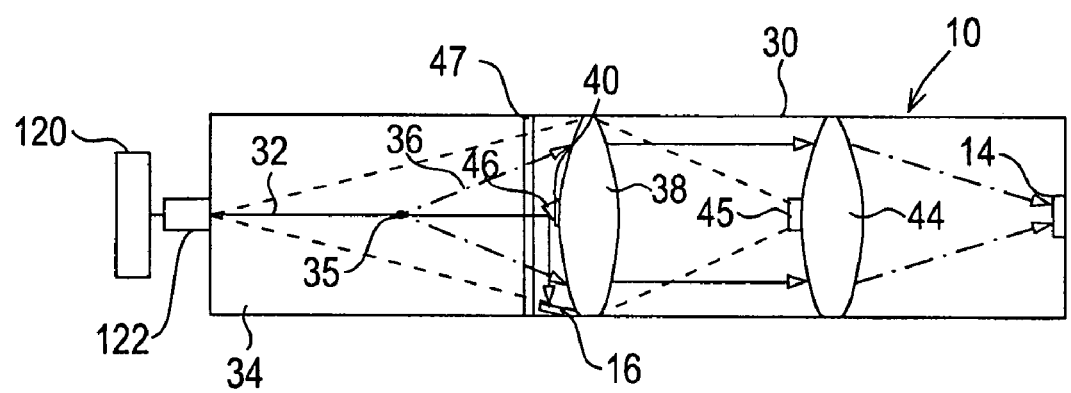
FIG. 9 is a view similar to FIG. 8 of a waterborne particle detector according to the FIG. 8 alternative embodiment of the invention in which an UV LED according to the FIG. 7 or 7A embodiments is employed in place of the laser light source.

In another embodiment of the invention, an LED is employed as the light source in place of the laser diode. Using an LED as the light source has advantages over a laser including longer lifetime, lower device cost, and reduced speckle. The electronic requirements and shielding requirements for LEDs also are less stringent than that for lasers. However, an LED is a relatively diffuse light source with a light emission angular distribution typically much larger than that of a laser diode. Accordingly, when an LED is used additional optics are necessary to focus and collimate the light beams. FIG. 9 shows an optical unit, an LED light source 120 and optical lens 122 instead of a laser. FIG. 7 illustrates a simplified optical path using an LED 120 as the light source in an airborne particle detector in accordance with the present invention. As seen in FIG. 7, an optical lens assembly 122 is placed in front of the LED light source 120 between the LED 120 and the flow cell 100. Optical lens assembly 122 comprises a plurality of lenses which together shape the light beam from the LED 122 into a near-collimated light beam 124 which is concentrated on the flow cell 100. Alternatively, as shown in FIG. 7A, the optical lens 126 may be designed to focus the light beam 128 on or near the first lens 38 of the Mie scattering particle size detector which is similar to the Mie particle size detector discussed previously. Various LEDs are available commercially that emit over a desired wavelength range and advantageously may be employed an in airborne particle detector of the present invention.

Figure 8:
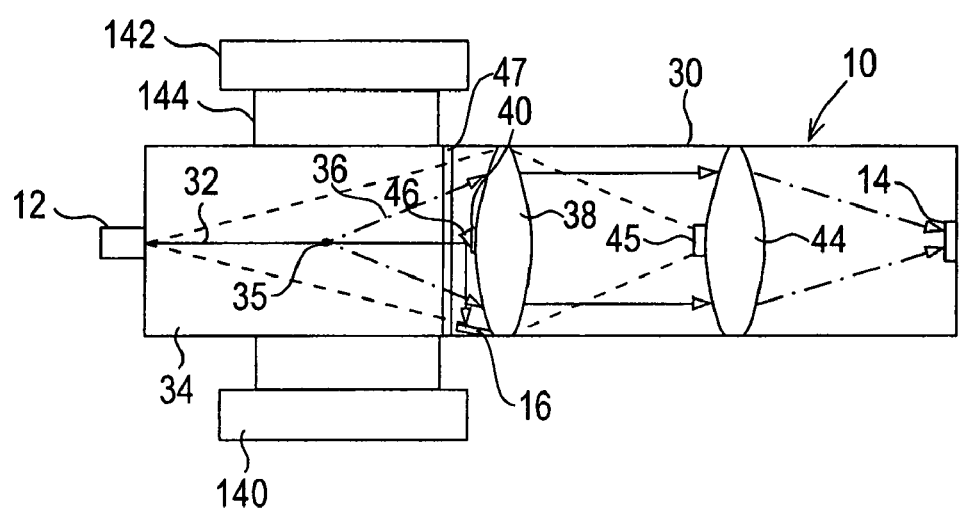
FIG. 8 is a view similar to FIG. 1 of a particle detector according to an alternative embodiment of the invention specifically designed for detecting waterborne particles.

Other embodiments are possible. For example, referring to FIG. 8, the above described airborne particle detector may be modified for use for detection of waterborne particles by providing water tight inlet and outlet couplings 140, 142 at the inlet and outlet ends of the sample cell 34, and a peristaltic or scroll pump 144 in place of the fan 37. Since waterborne particles of interest, i.e., bacteria or bacterial spores may have a size range of about 1 to 20 μm, the dimensions of beam diverting member 40 should be adjusted accordingly.

Figure 11:
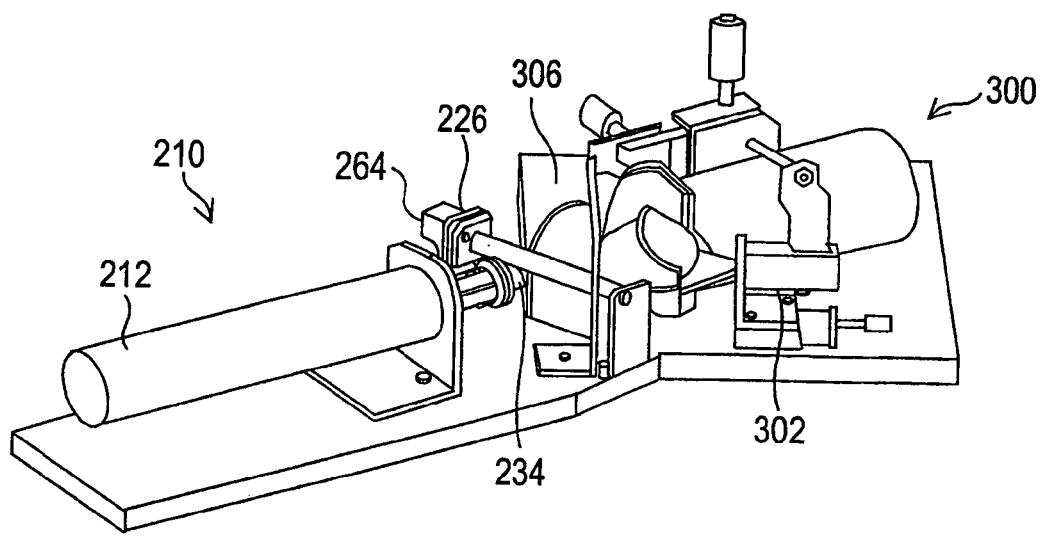
FIG. 11 is a perspective view and FIG. 12 is a schematic view of an airborne pathogen detector and characterization system according to another embodiment of the present invention.
Figure 12:
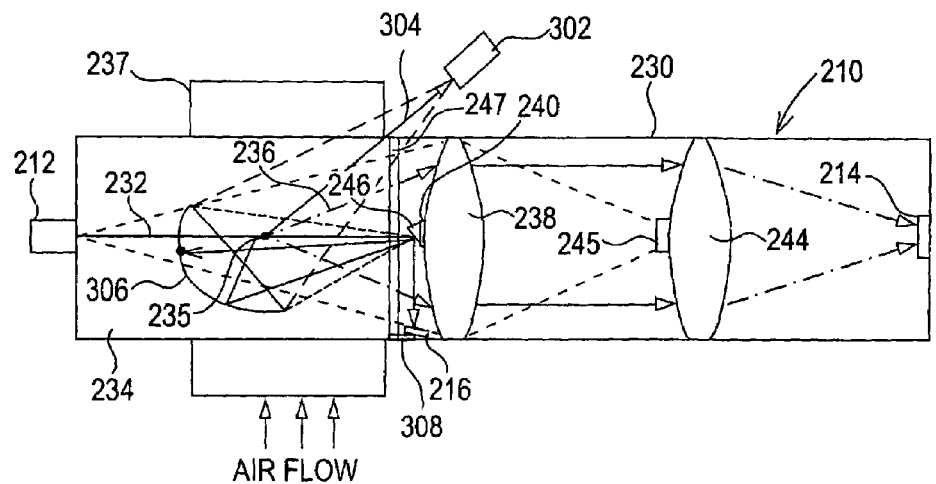
Figure 13:
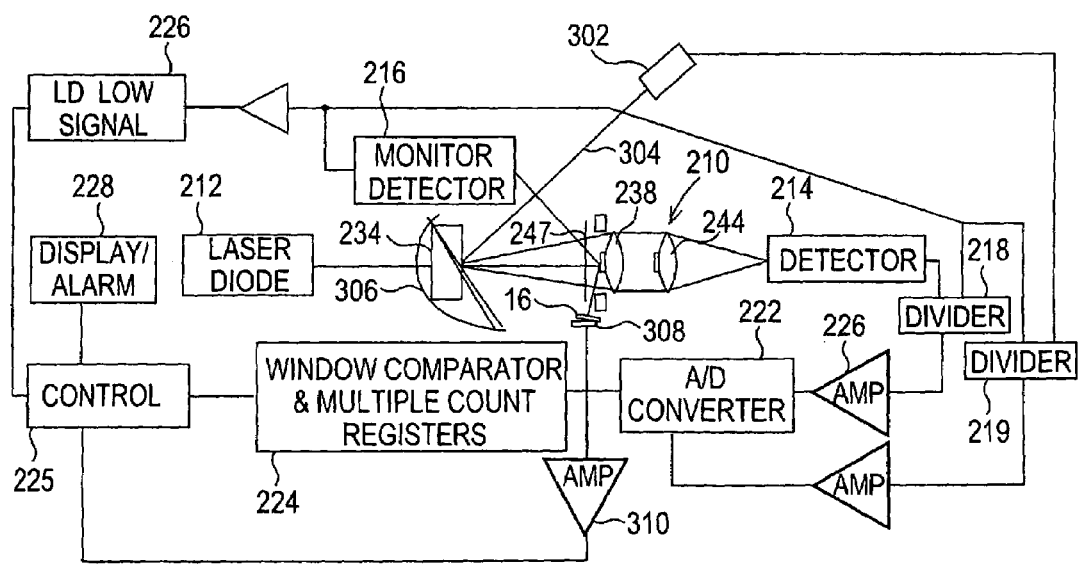
FIG. 13 is a schematic block diagram of an airborne pathogen detector and characterization system according to another preferred embodiment of the invention.
Figure 14:
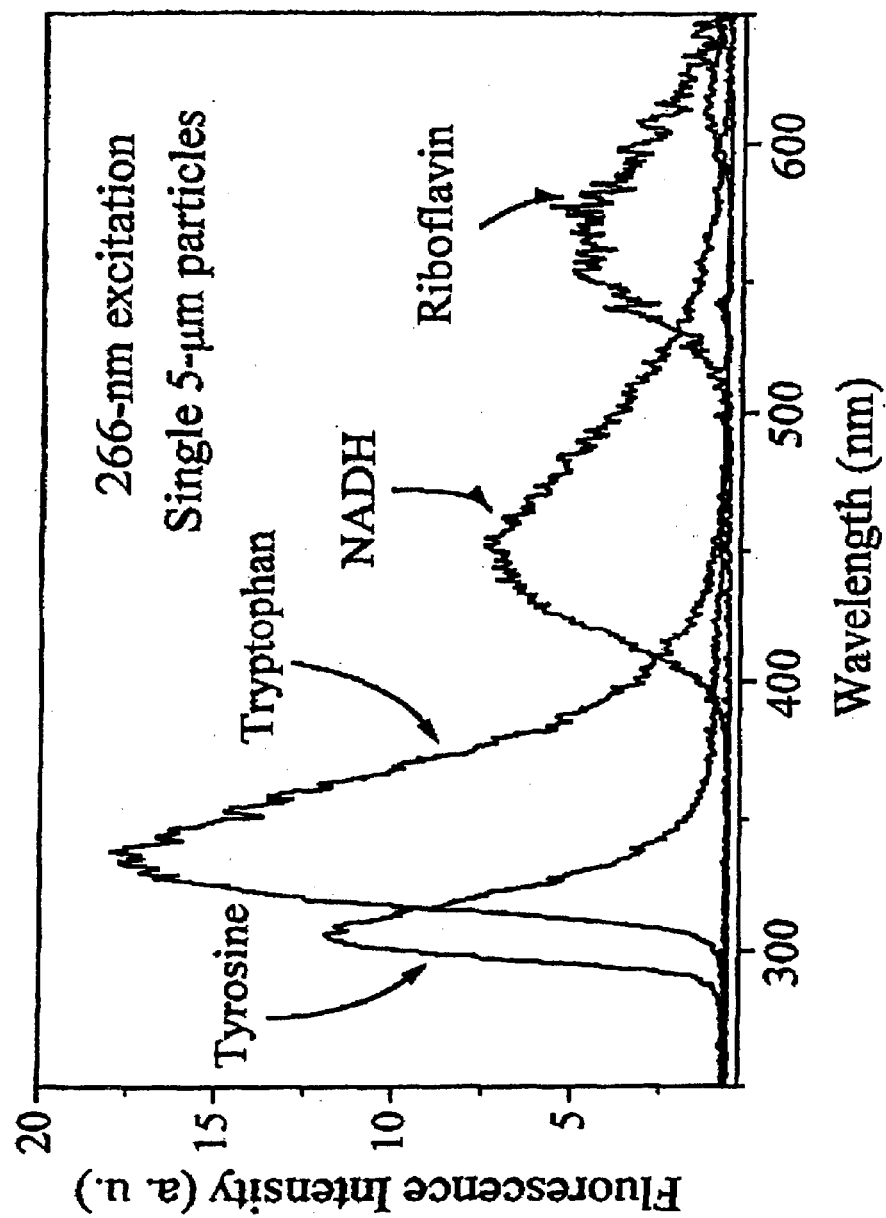
FIGS. 14-17 are graphs illustrating the relationship of wavelength to relative fluorescence intensity of tyrosine, tryptophan, nicotinamide adenine dinucleotide (NADH) and riboflavin; spores, road dust, ammonium nitrate, ammonium sulfate, carbon black; saccharomyees cerevisial aerosols; and diesel exhaust, respectively.
Figure 15:
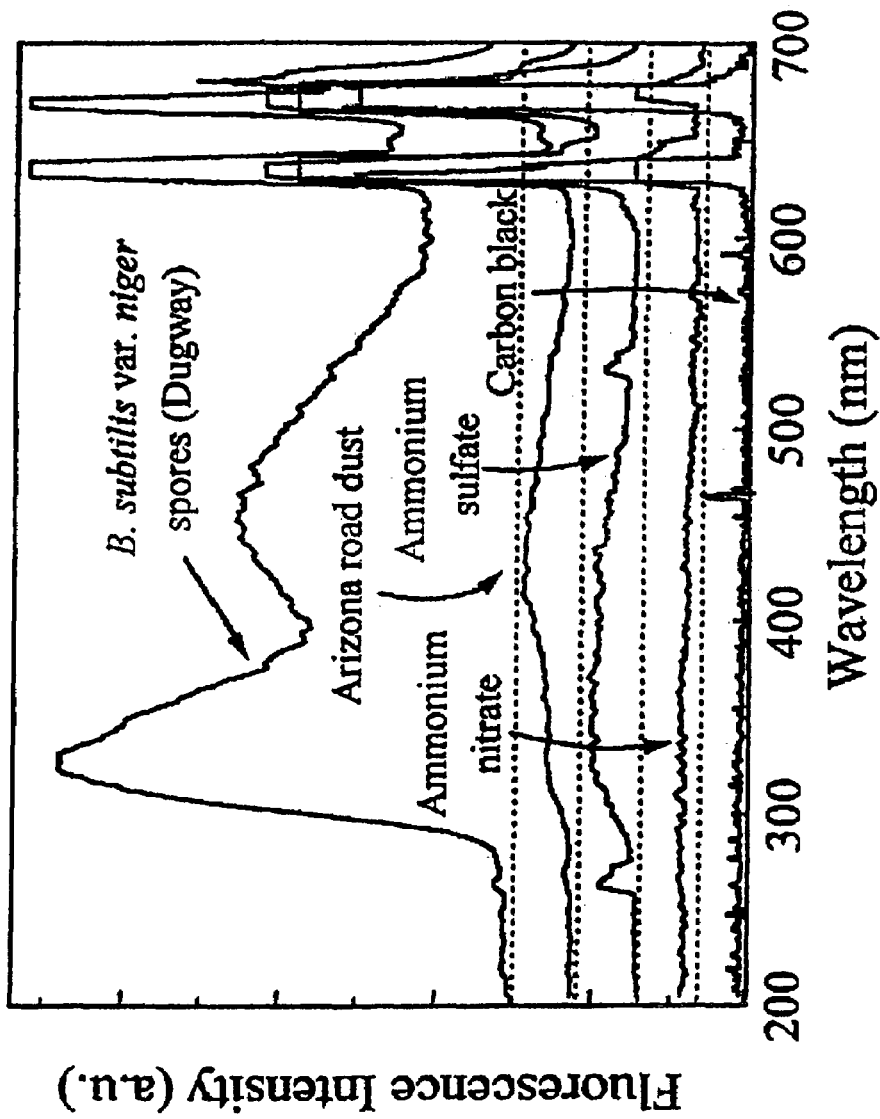
Figures 16, 17:
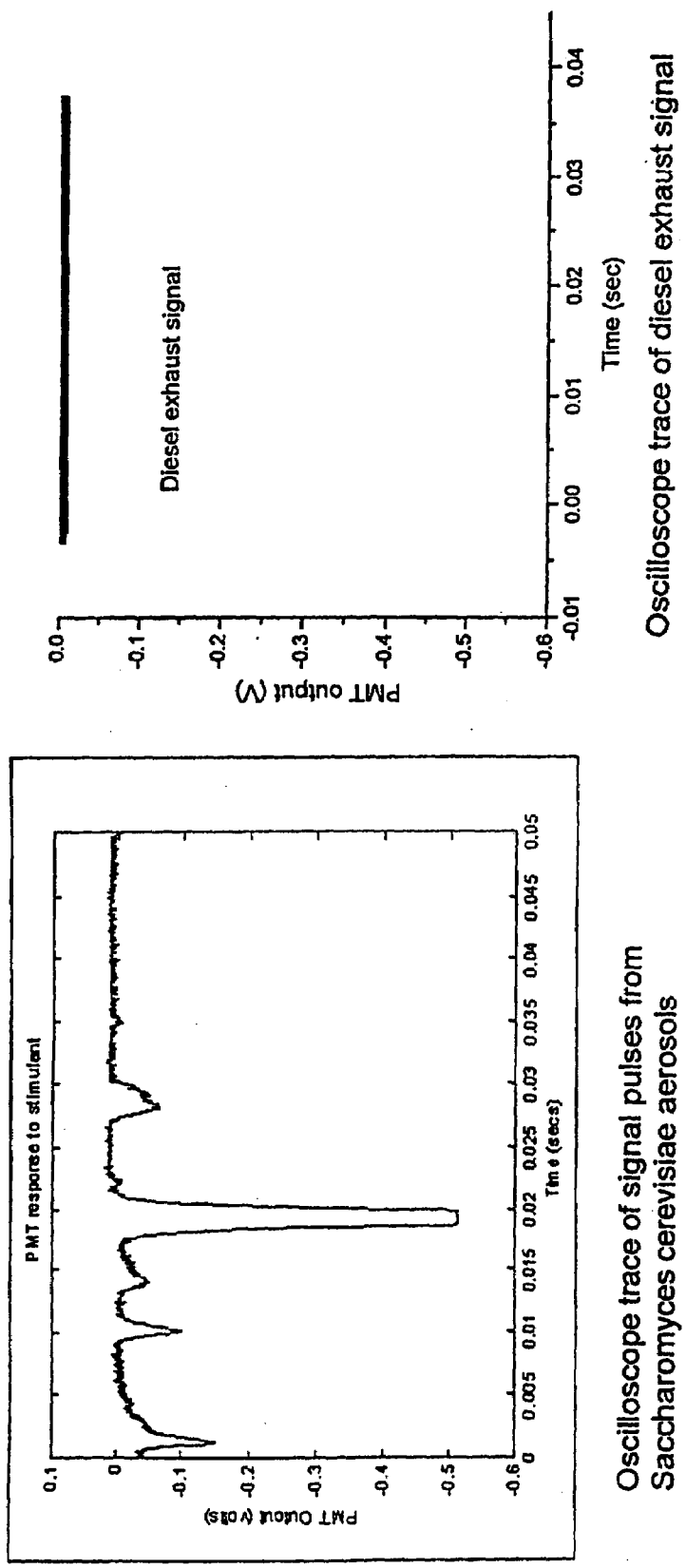
Figure 18:
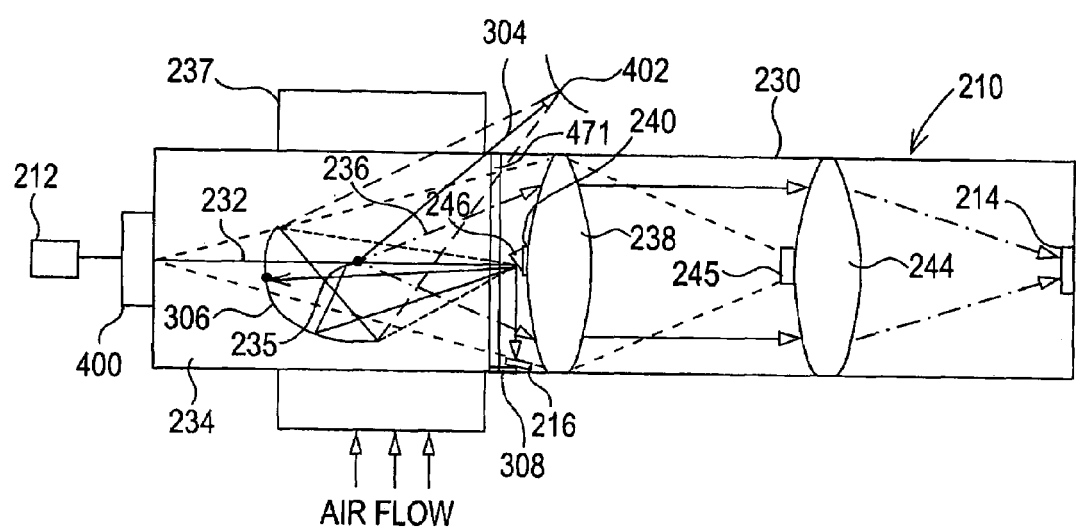
FIG. 18 is a view similar to FIG. 12 of an airborne pathogen detector and characterization system according to another preferred embodiment of the present invention.

Referring first to FIGS. 11, 12 and 13, the system for detection and identification of airborne or waterborne biological agents fluorescence in accordance with an additional embodiment of the invention comprises a first optical unit 210 for detecting particles of a selected particle size, e.g., approximately 1 to 7 microns, and a second optical unit 300 for discriminating between biological toxins or biological agents and inorganic particles. The first optical unit 210 comprises a laser diode or other light source 212 for directing a light beam into the optical unit, a first photodetector 214 at the output of optical unit for detecting light transmitted through the unit, a second photodetector 216 for detecting the light output of the laser diode, a differential amplifier 218 for dividing the output of photodetector 214 by the output of photodetector 216, an amplifier 226 connected to the output of differential amplifier 218, an analog to digital converter 222, a window comparator circuit 224, and a control and output display unit 225 connected to the output of circuit 224. A low signal detection circuit 226 is connected to the output of photodetector 216 which detects the laser diode power, and the output of circuit 226 is also connected to control unit 225. An alarm device 228 is also connected to control 225. The sample region in this exemplary embodiment is the same as previous described for other embodiments with reference to FIG. 1A.

Referring in particular to FIGS. 11-13, the second optical unit 300 includes an excitation laser 212 operating in a wavelength of a selected wavelength range, e.g., about 370 nm to about 410 nm. Laser 212 directs a collimated laser light beam 232 through the air sample region 234 within the housing. Laser 212 should be sufficiently intense (with fluence of, for example, about 0.03 Joules/cm$^2$) to excite measurable fluorescence in single particles that contain even only a few picograms of material. When the collimated light beam from laser 212 strikes biological particles within the air sample, if the particles contain a biological material such as, for example, riboflavin, and/or NADH, the particles will exhibit a fluorescence signal, which is collected via an elliptical mirror 306 located surrounding region 234, in part, and focused onto a fluorescence detector 302. Laser 212, mirror 306, and detector 302 are all fixedly positioned to the housing. The choice of elliptical mirror is made by considering its ability to focus light emanating from one of the foci onto the other one. In this configuration, the elliptical mirror serves as an efficient collector of fluorescence light from the bio-aerosol (at the first focal point of the ellipsoid) for a photo-detector located at the second focal point of the same ellipsoid. A parabolic mirror or other reflective element also could be used.

In a preferred embodiment of the invention, the alarm will be activated only after two conditions are met: (1) a sudden increase in the number of airborne particles within a predetermined size range (about 1 to about 7 nm) is detected; and (2) biological organisms or biological agents or organic materials are detected using, e.g., laser induced fluorescence as described below.

By themselves, particle size sensors are vulnerable to false alarms from ambient particulates. To further reduce these false alarms, the pathogen detector system of this embodiment is a biological organism or biological agent verification detector combining the particle sizing capability with an UV light-induced fluorescence sensor to discriminate between biological and non-biological particles. The pathogen detector system of the present invention also preferably includes a second optical unit 300 which includes a laser induced fluorescent sensor to detect metabolites which are present in biological organisms or biological agents, including biological warfare agents. More particularly, the second optical unit 100 includes an excitation laser operating in a wavelength of about 270 nm to about 410 nm, preferably about 370 nm to about 410 nm. A wavelength of about 270 nm to about 410 nm is chosen based on the premise that bio-agents comprise three primary metabolites: tryptophan, which normally fluoresces at about 270 nm with a range of about 220 nm-about 300 nm; nicotinamide adenine dinucleotide (NADH) which normally fluoresces at about 340 nm (range about 300 nm-about 400 nm); and riboflavin which normally fluoresces at about 400 nm (range about 320 nm-about 420 nm). Preferably, however, we prefer to use an excitation laser with a wavelength of about 370 to about 410 nm. This ensures excitation of two of the three aforesaid primary metabolites, NADH, and riboflavin in bio-agents, but excludes excitation of interference such as diesel engine exhaust and other inert particles such as dust or baby powder. Thus, in a preferred embodiment the present invention makes a judicial selection of wavelength range of the excitation light source, which retains the ability of exciting fluorescence from NADH and riboflavin (foregoing the ability to excite tryptophan) while excluding the excitation of interferents such as diesel engine exhaust. This step is taken to reduce false alarms generated by diesel exhaust (which can be excited by short UV wavelengths such as 266 nm light).

The output from fluorescence detector 302 is connected to a divider 219 which in turn is connected via an amplifier 227 and A/D converter 222 to control 225 which in turn is connected to display and alarm 228.

As in the case of the previously described embodiment, the pathogen detector may be implemented as a battery powered portable, hand-held detector for field personnel, and include a display for the current particle counts for each particle size and for signaling when fluorescencing metabolites are detected. It may also incorporate an audible alarm and a warning light for laser low power condition, and, if desired, a transmitter for sending signals to a base station. A stand-alone, desk top version may also be provided for use in office buildings or the like. This will be similar to the field version, but may be powered from a standard electrical wall socket via an AC/DC converter. In the latter case, the detector may be used to provide protection from bio-agent contaminated letters or packages in office desk top settings.

This embodiment of the invention is susceptible to modification. For example, a single laser source operating at a wavelength of about 370 nm to about 410 nm may be employed with an optical splitter in place of separate light sources for particle size count and fluorescence excitation. In addition, the invention may be employed as a fluorescence particle sizing biosensor for waterborne pathogen detection. Waterborne pathogens may be either bacteria or bacterial spores. Accordingly, the size range of waterborne pathogens is somewhat wider than for airborne pathogens, typically from about 1 to about 20 microns.

Figure 19:
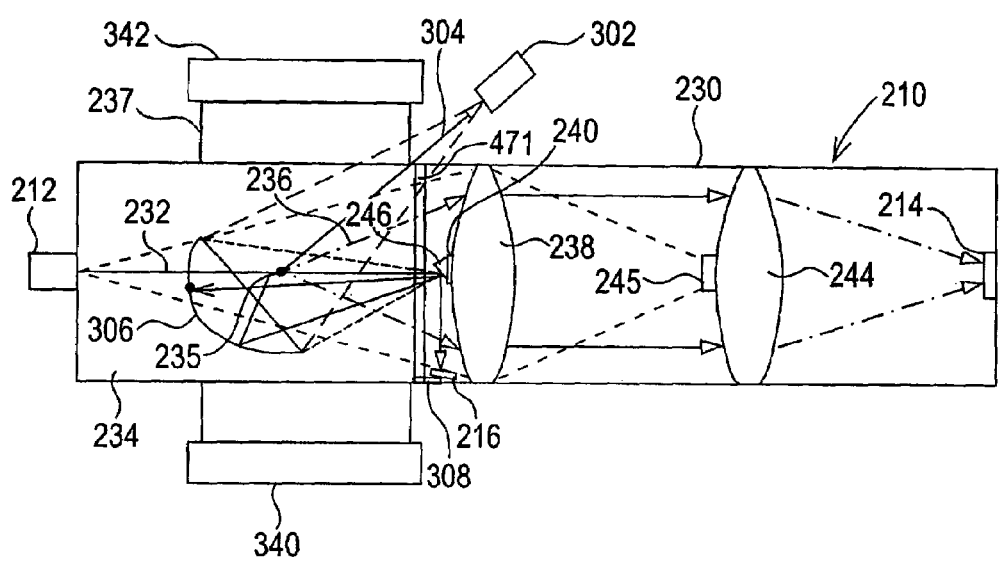
FIG. 19 is a view similar to FIG. 18 of waterborne pathogen detector according to another embodiment of the invention.
Figure 20:
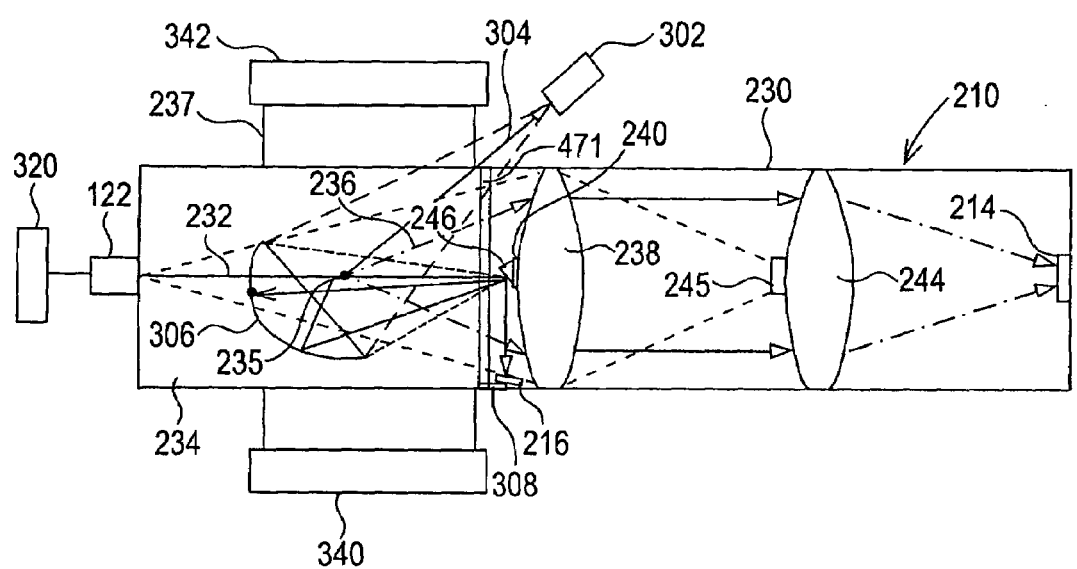
FIG. 20 is a view similar to FIG. 19 in which an UV LED is employed in place of the laser light source.

Referring to FIGS. 19 and 20, the device which is similar to the device of FIG. 11 may be modified for use for waterborne pathogen detection by providing water tight inlet and outlet couplings 340, 342 to the sample region 234, and a peristaltic or scroll pump 324.

In previous embodiments, an optical system with a sensing fluorescence emission detector is used to analyze metabolites. Microbes (bacteria, fungi etc) contain certain chemical compounds (metabolites) involved in metabolism. Tryptophan, pyridoxine, NADH, and riboflavin are among the major metabolites in microbes. Since these different metabolites have different excitation wavelength ranges from optimal excitation, it is advantageous to have a scheme for employing multiple lasers with different excitation wavelengths. The following are rationales for the multiple wavelength scheme: 1) to optimize the excitation efficiency by targeting the maxima of different metabolites fluorescence excitation curve; 2) since different types of bacteria (or other microbes) have different ratios of composition of metabolites in their cells, the multiple wavelength excitation will be able to get the information about the relative compositions of the metabolites and enable us to do a coarse classification of the types of microbes.

Figure 24:
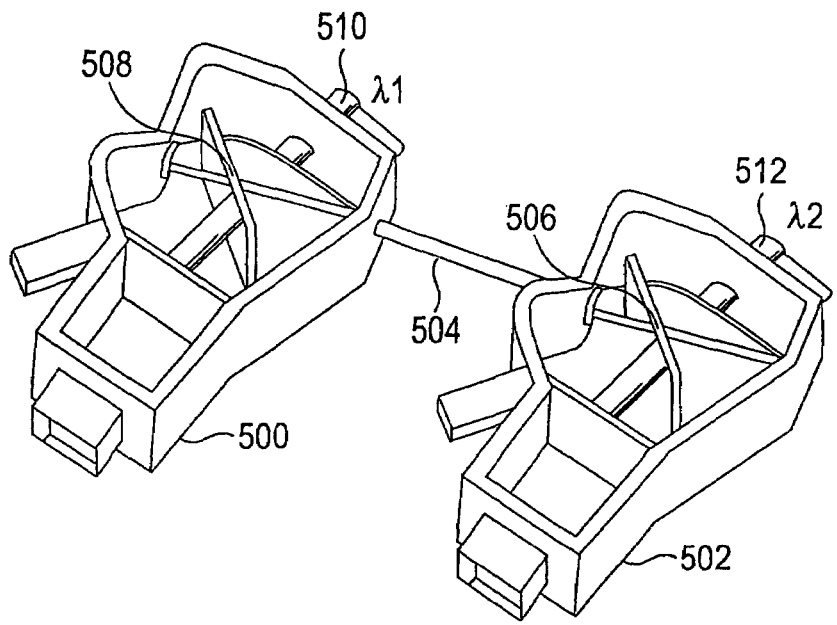
FIG. 24 is a schematic of a dual excitation laser wavelength tandem module design of the particle/fluorescence detector system according to an exemplary embodiment of the invention.

In order to have unambiguous analyses of the fluorescence emission from different metabolites in another preferred embodiment of the invention, a tandem modular design is used, in which a stream of particles passes through two fluorescence sensors 500, 502 (see FIG. 24) in tandem. Each sensor has a laser 510, 512 with different wavelengths (tuned to optimal excitation wavelength of various metabolites). As an example of the preferred embodiment: 405 nm laser wavelength is suitable for riboflavin, and 330-380 nm laser wavelength range is optimal for NADH. Two modules of the fluorescence sensors as shown in FIG. 24 (sensor 500 and sensor 502 having laser wavelengths of 405 nm and 340 nm respectively) are placed in series with a common airflow tube 504, which passes through the particle sensing regions 506, 508 of both sensors. Sensor 500 and sensor 502 will optimally detect the presences of riboflavin and NADH respectively. FIGS. 21-22 show the fluorescence emission verses excitation wavelength curve shown from: J.-K. Li et al, "Monitoring cell concentration & activity by multiple excitation fluorometry" Biotechnology. Prog. Vol. 7, 21, 1991.

Alternatively, for optimal excitation of fluorescence from tryptophan or pyridoxine, the wavelength selection will be at 270 nm and 320 nm respectively.

The fluorescence detection of sensor 500 (or sensor 502) can be of the following types: 1) integrated overall fluorescence signal in the whole spectral range. In this case, the fluorescence signal from the metabolite will be sent to the photo-detector of the sensor after passing through a long-wavelength optical pass filter to eliminate the excitation laser light. The ratio between the signal strengths of sensor 500 and sensor 502 will indicate the relative abundance of two types of metabolites in each sensor. (For example, if 405 nm and 340 nm wavelengths are chosen for the two sensors, then the ratio of the overall fluorescence signals will be related to the relative abundance of riboflavin and NADH.) 2) Wavelength-selective elements in individual sensor do spectral analysis. In this case, the spectral analyses provided by two sensors will provide the fluorescence spectral information under different conditions of excitation (i.e. different wavelengths). In either case, the information gathered will be useful in classifying the microbes.

Figure 23:
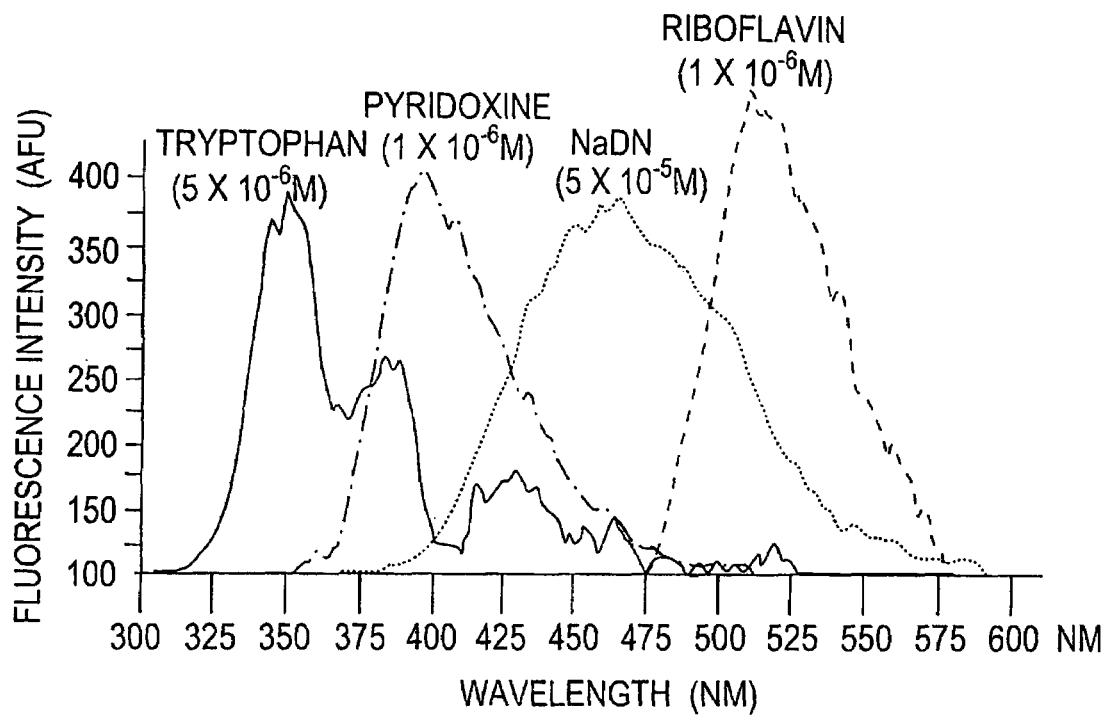
FIG. 23 is a graph of the fluorescence emission spectra for four metabolites excited by a Hg arc lamp.

FIG. 23 shows the fluorescence emission spectra of aforementioned four metabolites. Spectral analyses, especially those with different excitation wavelength, will enable the probing of the composition of microbes and use the resultant information for the purpose of microbial detection and classification.

The schematic of the sensor with two chambers is shown in FIG. 24. Design considerations for the multi-wavelength pathogen sensor include: 1) each sensor unit in the tandem configuration is a self-contained fluorescence/particle size sensor with a specific wavelength optimized to a target metabolite compound. 2) Two sensors 500, 502 share the same airflow tube or passageway 504, as shown in FIG. 24. The airborne particles in the airflow pass 504 through the sensing region 506, 508 of the sensors in sequence. The two sensors 500, 502 measures the same batch of airborne particles in a serial manner, it is therefore desirable to correlate the fluorescence signals from theses two sensors. One way to do this correlation is to use particle size measurement data from both sensors to pair up the fluorescence signals from two sensors, under the assumption that in the short time period for particles to transport from sensor 500 to sensor 502 the distribution of particle sizes is not significantly changed. 3) As a variation of the current fluorescence/particle size sensor design, two lasers might be used in each sensor: a laser common to sensor 500 and sensor 502 (e.g. a red 630 nm laser diode) is used to do particle size measurement to ensure a uniform way of determining particle size whereas an excitation laser (different one for sensor 500 and sensor 502 respectively) is used to excite fluorescence from metabolites. The reason for using a common laser wavelength for both sensors is to ensure a consistent particle size measurement so that the fluorescence signals from these two sensors can be correlated correctly based on the particle size information. This arrangement is to avoid the possibility of skewing the size measurement by the different absorption of the excitation light by the particles. While this exemplary embodiment uses two sensors and housings, a person skilled in the art would understand any number of housings or sensors may be used.

Figure 25:
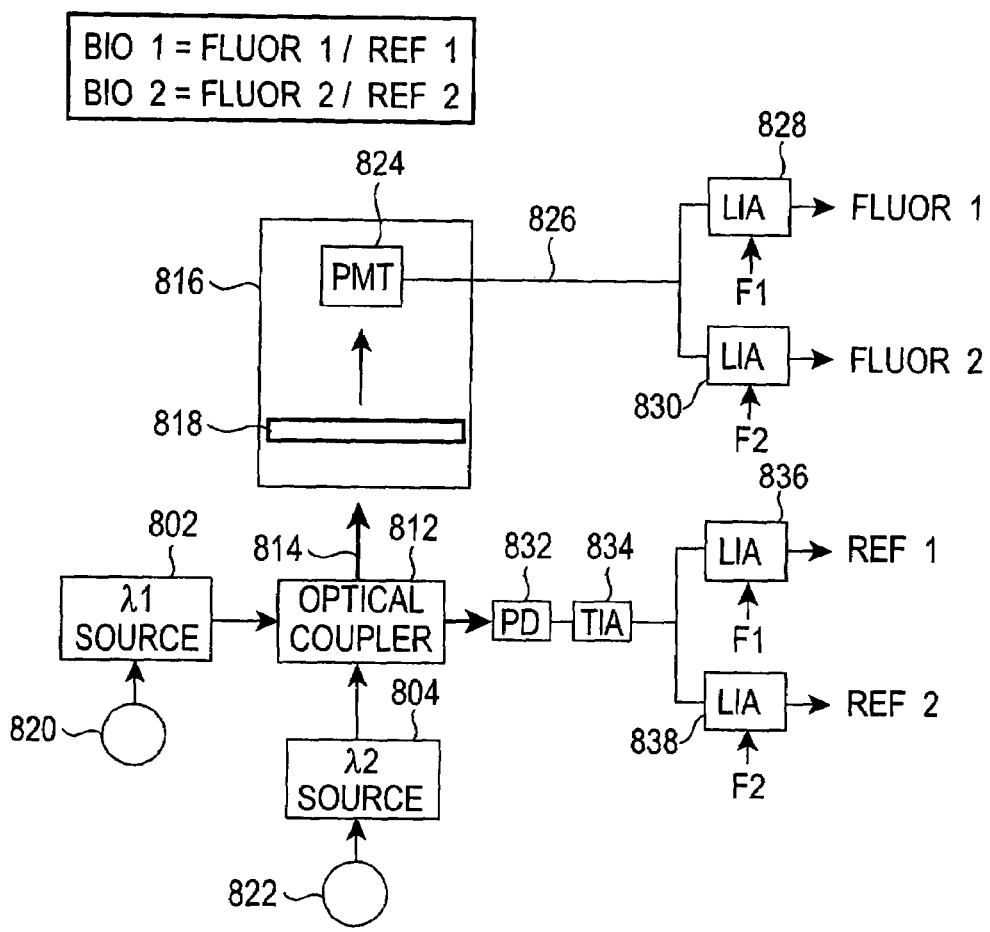
FIG. 25 is a schematic of a the particle/fluorescence detector system according to an exemplary embodiment of the invention in which two light beams are coupled to allow for the simultaneous measurement of two fluorescence signals.
Figure 26A:
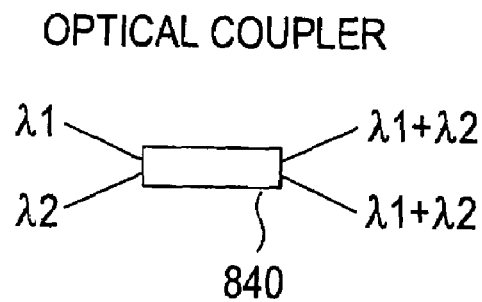
FIG. 26A-26B are examples of optical coupler for use in the particle/fluorescence detector system of FIG. 25.
Figure 26B:
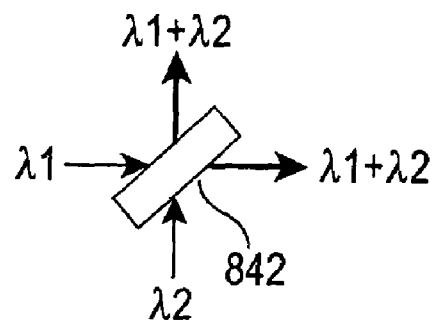
Figure 27:
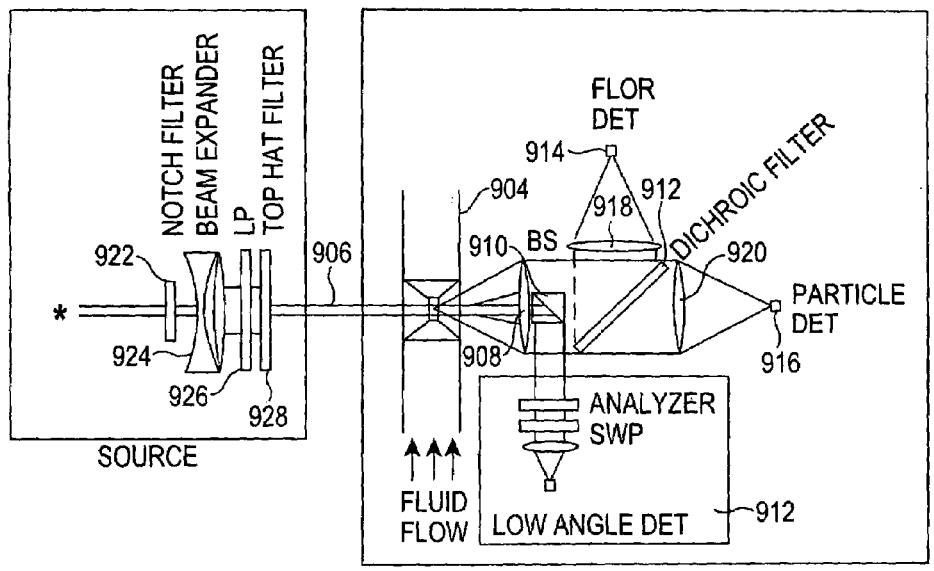
FIG. 27 is an is a schematic of another exemplary embodiment of the invention and an optics system to reduce noise in the light signal.
Figure 28:
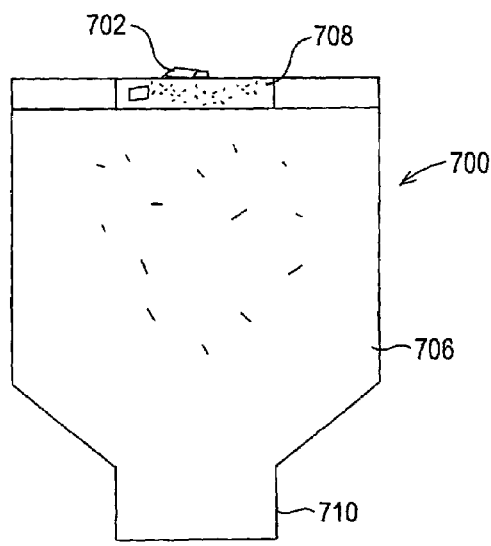
FIG. 28 is an exemplary embodiment of a testing system for use with the particle detector system.

In yet another embodiment of the present invention, two light beams are coupled to allow for the simultaneous measurement of two fluorescence signals. As shown in FIG. 25, two light sources 802, 804 are coupled through a optical coupler 812. The coupling can be done using either a fiber coupler 840 or a beam splitter 842, as illustrated in FIG. 26. The two combined light beams 814 intercept the incoming particles in the nozzle window opening 818 in the optical unit 816.

The two light sources 802, 804 are modulated at two distinct electrical frequencies (f1 and f2) by modulation units 820, 822. The modulation units 820, 822 can be achieved by internal electrical current modulation (if the two sources are, e.g., LED's or laser diodes) or external modulation by a mechanical chopper, an acousto-optical modulator or an electro-optical modulator.

In a preferred embodiment, a photomultiplier tube (PMT) 824 is used to detect fluorescence signals in the optical unit 816. The signal 826 out of the PMT is routed to two lock-in amplifiers 828, 830 tuned to respective modulation frequency (f1 or f2). In this scheme, the signal with modulation frequency f1 is originated from excitation wavelength λ1 and the signal with modulation frequency f2 is originated from excitation wavelength λ2. With differently modulated incident light beams and corresponding lock-in amplifiers, although the fluorescence signals from two excitation sources are mixed optically, they have different modulation frequencies (f1 and f2 respectively), therefore they are electronically distinct and readily differentiable by the two lock-in amplifiers 828, 830. The two signal outputs from lock-in amplifiers 828, 830 are FLOUR1 and FLOUR2 respectively.

Likewise, at the optical coupler, a portion of the beam is split off and sent to a photodetector 832. The photodetector 832 converts the light to a current signal and then an amplifier 834 such as a trans-impedance amplifier (TIA) converts the current signal to a voltage signal. Amplifiers 836, 838 finally selectively amplifies the signal having a specific modulating frequency to create REF1 and REF2 signals. The REF1 and REF2 signals are then subtracted from the FLOUR1 and FLOUR2 signals, respectively, to create the fluorescence emission spectra for the particles in the sample.

Another embodiment of the invention involves modifying the florescence/particle size detector system based on simulations and experiments on the beam blocker in the fluorescence/particle size sensor. Previously patents and patent applications by Hamburger et al. have disclosed the use of a beam blocker to block the residual portion of the laser from interfering with the measurement of the scattered light from the particles.

In this embodiment of the present invention, different sizes of beam blockers are used to improve sensitivity of the fluorescence/particle size detector system. When the beam blocker size is increased, all the particles that would have been seen otherwise are still viewable, only with a reduced intensity. The beam blocker may be enlarged to block nearly the whole lens without significant reduction in the ability to measure particle over a wide range of sizes.

Furthermore, light scatter by the beam blocker can be collected and measured. For a very small beam blocker, the correlation between the scatter light and the particle size does not fit a simple relationship and was even non-monotonic under certain conditions. However, for a certain angle, the blocker reduced these inconsistencies and provided a very predictable relationship between particle size and collected scattered light. In addition, as the angle is increased the relationship remains basically unchanged except for a reduction in the amount of light collected. That is, the blocker tolerances are very relaxed as long as the blockers are larger than a minimum size and the relationship between particle size and collected light was highly predictable. This relationship between the particle size to the collected scatter light for larger beam blockers was fairly smooth and predictable, even with 10 and 20 μm particles. Therefore, placing a second detector in chamber to collect the light reflected off the beam blocker allows for another means of detecting the particle size.

Use of second detector is most advantageous in measure particle of the size 0.1 μm to 10 μm. Test and simulations have shown that the dynamic range needed measure particle down to 0.1 μm size along with the larger particle would require a dynamic range for the detectors that is hard to achieve. Blocked light could provide better sensitivity for measuring small particles and tests have shown an ideal point into which the break-up of the angular range of particles measured across the lens.

In this embodiment, the fluorescence/particle size detector system 900 does not have a beam blocker per se. However, as in previous embodiments, the light beam 906 enters the sample region 904 within the housing 902 and the beam is deflected off particles in the fluid flow. A lens 908 is located in the housing in the path of both the unscattered and scattered portions of the beam exiting the sample area 904. A blocking section 910 is placed behind the lens 908 to reflect, into low angle detection unit 912, the unscattered portion of the beam and the portion of light scattered at a low angle The low angle detection unit 912 includes a detector and optics to focus the beam and remove the unscattered portion of the beam before the beam enters the detector. The lower angle detector may be optimized to measure particles from 0.1 μm to 1 μm.

The housing 902 also contains a fluorescence detector 914 and a particle detector 916. A wavelength selective filter 912 such as a dichroic filter is positioned in path of the light beam behind the blocking section 910. The filter 912 selectively transmits light to the fluorescence detector 914 and the particle detector 916 through lens 918, 920 respectively. The particle detector 916 may be optimized to measure particles in the range of 1 μm to 10 μm or larger. By breaking up the ranges of particles and scattered intensities any one detector measure, the dynamic range needed for the detectors is reduced to a more achievable range.

This embodiment also includes optics to reduce the noise in the laser. These optics may be used with any embodiment of the invention. The residual noise reducing optics includes: a notch filter 922; a beam expander 924; a linear polarizer 926 and a top hat filter 928.

This concept of using multiple detectors can be extended to selecting arbitrary angular regions of the collecting lens to be redirected to separate detectors that correspond to an optimized region of particle sizes to detect. The limit of this would be using a camera to collect all the light and analyze the resulting image. Such an extreme is impractical, as the camera is much slower than individual detectors, requires more processing power, and is significantly more costly to implement. By keeping these zones to a minimum and comparing additional information like the intensity for the individual polarizations and the scattering at multiple wavelengths, it may be possible to achieve increased and new sensitivities.

Yet another embodiment of the current invention involves an improved testing system for the fluorescence/particle size sensor. To test the ability of the system to detect micron size particles, a test powder containing micron size particles must be injected into the sample region 34, as shown in FIG. 1. Traditionally, test powder is placed in a chamber and connected to the sample region 34. Air is then blown through the chamber to force the test particles to aerosolize and push the particles into sample region of the fluorescence/particle size sensor.

Typically, Arizona Road Dust is used for these tests. Arizona Road Dust has been used for testing filtration, automotive, and heavy equipment components for decades. A variety of names have been applied to Arizona Road Dust including Arizona Silica, AC Fine and AC Coarse Test Dusts, SAE Fine and Coarse Test Dusts, J726 Test Dusts, and most recently ISO Ultrafine, ISO Fine, ISO Medium and ISO Coarse Test Dusts. Arizona Road Dust consists of refined material that has settled out of the air in the Salt River Valley, Ariz. Examination of air floated dust particles from the Salt River Valley of Arizona reveals that it contains a high percentage of extremely fine particles, which are highly abrasive in nature and thus a good testing substitute for airborne pathogens, microbes, molds, biological warfare agents and dangerous dust. However, Arizona Road Dust and its alternatives have a tendency to clump together into large particles and interfere with testing and calibration of the detection system. Thus, a need exists for a system that limits the clumping of larger particles entering the sensor during testing and calibration.

In this embodiment of the test system, a particle size filter unit 700 is provided to the eliminate the problem of larger particles or clumps of particles entering the fluorescence/particle size detection system. A quantity of test powder 702 is placed on a filter medium 708, and the filter 700 is tapped in order to drive the particles into and through the filter into chamber 706 as shown in FIG. 28. The outlet end 710 of the chamber 706 is connected to the inlet end 102 of the sample region 34 from FIG. 1A. (See FIGS. 1 and 1A). The filter medium restricts the large unwanted particles or clumps of smaller particles from being delivered to the inlet 102 of the particle detector system.

The filter unit 700 comprises a size selective filter medium 708. Preferably, the filter medium 708 is a High Efficiency Particulate Air (HEPA) Filter. HEPA filters are required to remove 99.97% of 0.3 microns particles from the air. Thus, they are ideally suited for use in the testing system for the fluorescence/particle size detection system. However, the filter medium used is not limited to any one type of filter. Any filter medium that removes particles or clumps of particle above the minimum requirements of user is consistent with this embodiment of the invention.

It should be emphasized that the above-described embodiments of the present invention are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

The invention claimed is:

1. A detector system for detecting biological organisms or biological agents of predetermined particle size in a fluid comprising:

a housing having a passageway to allow for a fluid to flow through the housing;

a first light source for sending a light beam through the fluid in the passageway, whereby portions of the light beam are scattered at various angles by particles of various sizes present in the fluid, and wherein an unscattered portion of the light beam remains unscattered;

a first detector positioned to receive scattered portions of said light beam after said passageway for detecting and discriminating between particles of a selected size range in the fluid;

a lens receiving the light beam as it exits the passageway; and a reflector placed behind the lens to reflect the unscattered portion of the light beam and a portion of light beam scattered at a low angle, whereby the unscattered portion of the light beam and the portion of the light beam scattered at a low angle are received by a low angle detector;

a second light source for sending light through said fluid passing in the passageway for exciting fluorescence in the particles in said fluid; and a second detector positioned to receive light from said second light source for detecting fluorescence of said particles.

2. The apparatus of claim 1, wherein the first light source and a second light source comprise a single light source.

3. The fluorescence/particle detection system of claim 1, wherein each light source produces light with a different wavelength.

4. The fluorescence/particle detection system as claimed in claim 1, further comprising:

a light beam modulator in the path of the light before the fluid in the passageway to modulate the first and second light beams at different frequencies; and an control mechanism to differentiate the first and second light beams based on the modulation frequency of the light beams and to produce measurement of multiple fluorescence signals.

5. The fluorescence/particle detection system of claim 4, wherein a portion of the beam is split off at the light beam modulator to create a reference signal for measuring the fluorescence of said biological organisms or biological agents.

6. The fluorescence/particle detection system of claim 4, further comprising a control mechanism to differentiate the first and the second light beams based on the modulation frequency of the beams and to produce measurement of multiple fluorescence signal.

7. The apparatus of claim 1, wherein the fluid comprises air.

8. The apparatus of claim 1, wherein the fluid comprises water.

9. The apparatus of claim 1, wherein the fluid comprises air and the particles are of size from about 1 to about 7 microns.

10. The apparatus of claim 1, wherein the fluid comprises water and the particles are of size from about 1 to about 20 microns.

11. The apparatus of claim 1, wherein the second light source operates at a wavelength of about 270 nm to about 410 nm.

12. The apparatus of claim 1, wherein the second light source operates at a wavelength of about 370 nm to about 410 nm.

13. The fluorescence/particle detection system of claim 1, wherein each light source is tuned to produce light of an optimal excitation wavelength of one or more metabolites.

14. The fluorescence/particle detection system of claim 1, wherein the wavelength of one light source is suitable for detecting riboflavin.

15. The fluorescence/particle detection system of claim 1, wherein the wavelength of one light source is suitable for detecting NADH.

16. The fluorescence/particle detection system of claim 1, further comprising a long-wavelength optical pass filter in the path of the light beam before the fluorescence sensor to eliminate excitation laser light.

17. The fluorescence/particle detection system of claim 1, wherein said detector contains wavelength-selective elements for spectral analysis of the light.

18. The fluorescence/particle detection system of claim 1, wherein said plurality of sensors measure the fluorescence of the same batch of fluid.

19. The apparatus of claim 1, further comprising an elliptical mirror for collecting fluorescence light signals generated at one of the foci of the ellipsoid and directing the collected fluorescence light signals to a photo-detector located at the other focus of the ellipsoid.

20. The apparatus of claim 1, further comprising a control circuit connecting to outputs from said first and second detectors for generating an alarm output signal under selected conditions.

21. A detector system for detecting biological organisms or biological agents of predetermined particle size in a fluid comprising:
  a housing having a passageway to allow for a fluid to flow through the housing;
  a first light source for sending a light beam through the fluid in the passageway, whereby portions of the light beam are scattered at various angles by particles of various sizes present in the fluid, and wherein an unscattered portion of the light beam remains unscattered;
  a first detector positioned to receive scattered portions of said light beam after said passageway for detecting and discriminating between particles of a selected size range in the fluid;
  a lens receiving the light beam as it exits the passageway; and
  a reflector placed behind the lens to reflect the unscattered portion of the light beam and a portion of light beam scattered at a low angle, whereby the unscattered portion of the light beam and the portion of the light beam scattered at a low angle are received by a low angle detector.

22. The fluorescence/particle detection system of claim 21, further comprising:
  a second light source for sending light through said fluid passing in the passageway for exciting fluorescence in the particles in said fluid; and
  a second detector positioned to receive light from said second light source for detecting fluorescence of said particles.

23. The apparatus of claim 21, wherein the fluid comprises air.

24. The apparatus of claim 21, wherein the fluid comprises water.

25. The apparatus of claim 21, wherein the fluid comprises air and the particles are of size from about 1 to about 7 microns.

26. The apparatus of claim 21, wherein the fluid comprises water and the particles are of size from about 1 to about 20 microns.

27. The apparatus of claim 21, further comprising an elliptical mirror for collecting fluorescence light signals generated at one of the foci of the ellipsoid and directing the collected fluorescence light signals to a photo-detector located at the other focus of the ellipsoid.

28. The apparatus of claim 21, further comprising a control circuit connecting to outputs from said first and second detectors for generating an alarm output signal under selected conditions.

* * * * *